United States Patent
Tsuji et al.

(10) Patent No.: US 10,004,448 B2
(45) Date of Patent: Jun. 26, 2018

(54) OSTEOPOROSIS DIAGNOSTIC SUPPORT APPARATUS

(71) Applicants: Media Co., Ltd., Tokyo (JP); Gifu University, Gifu (JP)

(72) Inventors: Hironobu Tsuji, Tokyo (JP); Yosuke Tsuji, Tokyo (JP); Tatsuro Hayashi, Tokyo (JP); Hiroshi Fujita, Gifu (JP); Takeshi Hara, Gifu (JP); Chisako Muramatsu, Gifu (JP); Kazuki Horiba, Gifu (JP); Akitoshi Katsumata, Gifu (JP)

(73) Assignee: Media Co., Ltd., Tokyo (JP)

( * ) Notice: Subject to any disclaimer, the term of this patent is extended or adjusted under 35 U.S.C. 154(b) by 0 days. days.

(21) Appl. No.: 15/162,447

(22) Filed: May 23, 2016

(65) Prior Publication Data

US 2016/0262686 A1    Sep. 15, 2016

Related U.S. Application Data

(63) Continuation-in-part of application No. PCT/JP2014/081056, filed on Nov. 25, 2014.

(30) Foreign Application Priority Data

Nov. 25, 2013 (JP) .................... 2013-242678

(51) Int. Cl.
*A61B 8/00* (2006.01)
*A61B 5/00* (2006.01)
(Continued)

(52) U.S. Cl.
CPC .......... *A61B 5/4509* (2013.01); *A61B 5/0088* (2013.01); *A61B 5/4542* (2013.01);
(Continued)

(58) Field of Classification Search
CPC .............................. A61B 6/505; G06T 7/0012
See application file for complete search history.

(56) References Cited

U.S. PATENT DOCUMENTS

| | | | |
|---|---|---|---|
| 2006/0239532 A1* | 10/2006 | Taguchi | ............... G06T 7/0012 382/132 |
| 2007/0286467 A1 | 12/2007 | Asano et al. | |
| 2014/0009573 A1 | 1/2014 | Fujita et al. | |

FOREIGN PATENT DOCUMENTS

| | | |
|---|---|---|
| GB | 2436980 A | 7/2010 |
| JP | 3964795 B2 | 8/2007 |

(Continued)

OTHER PUBLICATIONS

Takuya Matsumoto et al., "Osteoporosis screening by use of automated scheme for measuring mandibular cortical thickness on dental panoramic radiographs," IEICE Technical Report, Jan. 12, 2012, MI, Medical Imaging, 111 (389), pp. 325 to 329.

(Continued)

*Primary Examiner* — Michael D Abreu
(74) *Attorney, Agent, or Firm* — Manatt, Phelps & Phillips, LLP

(57) ABSTRACT

Provided is an apparatus for measuring the thickness, roughness, and morphology index of the mandibular cortical bone using a dental panorama image to assist in the diagnosis of osteoporosis, wherein the thickness, roughness, and morphological index of the cortical bone is measured more accurately and the diagnosis of osteoporosis can be supported more accurately. An osteoporosis diagnostic support apparatus, wherein the apparatus has a contour extraction unit adapted to extract a mandibular contour from an image of a mandibular cortical bone photographed by a photographic apparatus adapted to photograph the mandibular cortical bone and surroundings thereof, a line segment extraction unit adapted to extract line segments from the (Continued)

image of the mandibular cortical bone photographed by the photographic apparatus; and a cortical bone thickness calculation unit adapted to calculate a thickness of the cortical bone based on the extracted mandibular contour and line segments.

6 Claims, 16 Drawing Sheets

(51) Int. Cl.
  *A61B 6/00*   (2006.01)
  *G06T 7/00*   (2017.01)
  *G06T 7/12*   (2017.01)
  *G06T 7/149*  (2017.01)
  *G06T 7/62*   (2017.01)

(52) U.S. Cl.
  CPC ............ *A61B 5/7278* (2013.01); *A61B 6/501* (2013.01); *A61B 6/505* (2013.01); *A61B 6/5217* (2013.01); *G06T 7/0012* (2013.01); *G06T 7/12* (2017.01); *G06T 7/149* (2017.01); *G06T 7/62* (2017.01); *A61B 2576/02* (2013.01); *G06T 2207/10116* (2013.01); *G06T 2207/20036* (2013.01); *G06T 2207/20116* (2013.01); *G06T 2207/30008* (2013.01); *G06T 2207/30036* (2013.01)

(56) References Cited

FOREIGN PATENT DOCUMENTS

| | | |
|---|---|---|
| JP | 4956745 B2 | 6/2012 |
| JP | 2012-143387 A | 8/2012 |
| JP | 2013-116293 A | 6/2013 |
| WO | 2006/043523 A1 | 4/2006 |
| WO | 2012/128121 A1 | 9/2012 |

OTHER PUBLICATIONS

Yukiyasu Yoshinaga et al., "Evaluation Method of Concentration Degree and Convergence Index Filter," Medical Imaging Technology, vol. 19, No. 3, May 2001, issued by The Japanese Society of Medical Imaging Technology.

Kazuki Horiba et al., "Automated Measurement of Mandibular Cortical Width on Dental Panoramic Radiographs for Early Detection of Osteoporosis: Extraction of Linear Structures," Medical Imaging Technology, Nov. 18, 2014, vol. 32, No. 5, pp. 342 to 346.

* cited by examiner

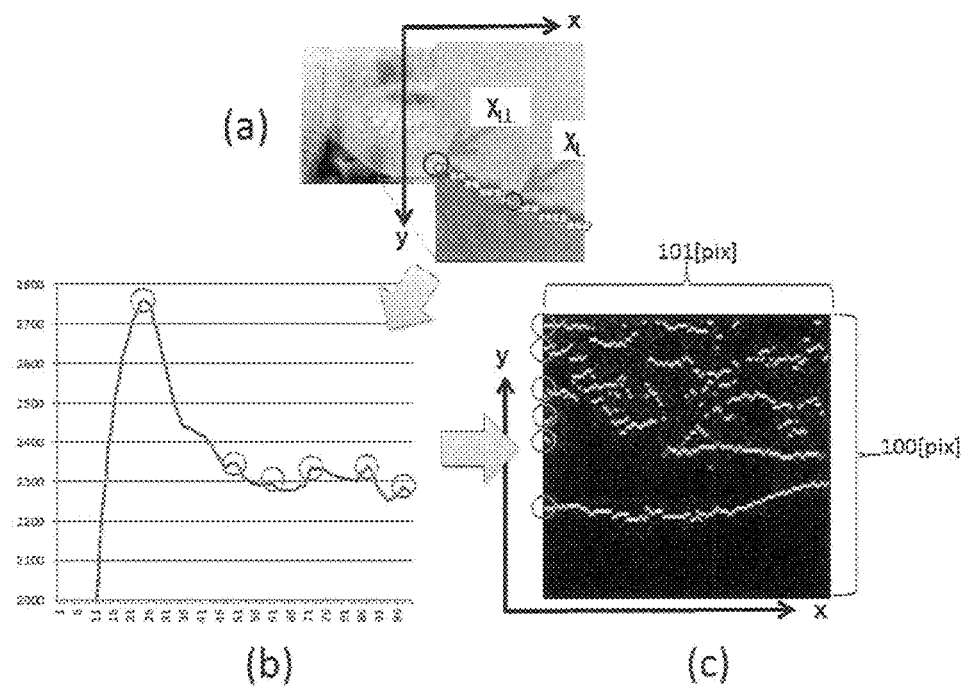
Figure 6
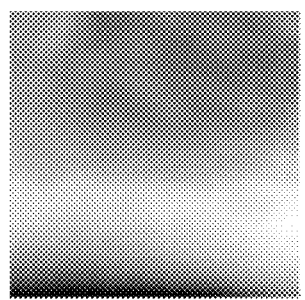
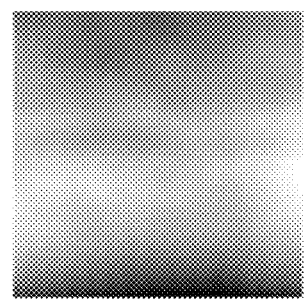
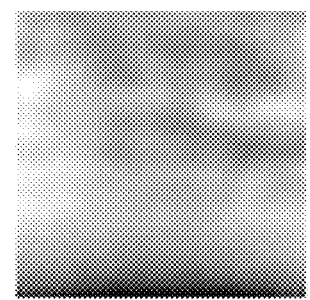
Figure 7A        Figure 7B        Figure 7C (a) (b)

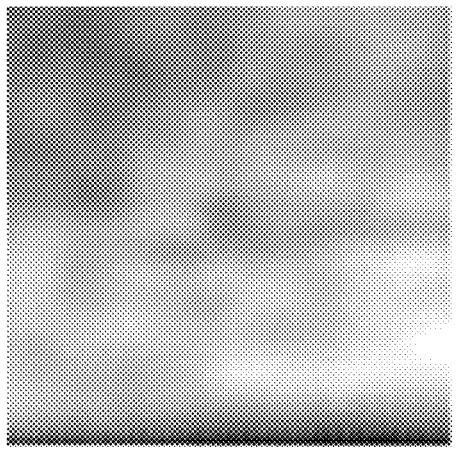 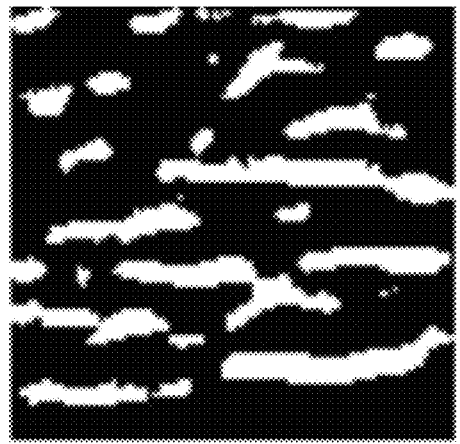
Figure 18A　　　　　　　　Figure 18B
 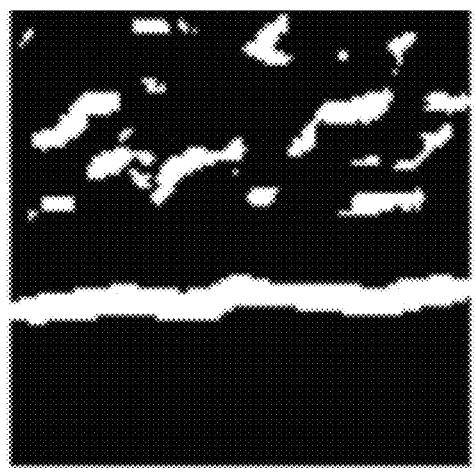
Figure 19A　　　　　　　　Figure 19B

| No. | I, II, III | (1) | (2) | (3) | (4) | (5) |
|---|---|---|---|---|---|---|
| 1 | I | 36.1 | 139.0 | 23.5 | 0.450254 | 3202.0 |
| 2 | I | 27.2 | 142.5 | 105.5 | 0.940662 | 3225.0 |
| 3 | I | 34.7 | 60.0 | 111.0 | 0.974139 | 3871.0 |
| 4 | I | 45.7 | 93.0 | 134.5 | 0.998045 | 2941.5 |
| 5 | I | 36.7 | 143.5 | 66.0 | 0.991810 | 2698.0 |
| 6 | I | 36.8 | 49.0 | 147.5 | 1.009794 | 3713.0 |
| 7 | I | 34.0 | 131.0 | 0.0 | 0.000000 | 2964.5 |
| 8 | I | 40.4 | 122.0 | 70.0 | 0.956717 | 2987.0 |
| 9 | I | 36.5 | 180.0 | 63.0 | 0.961339 | 2162.0 |
| 10 | I | 32.0 | 141.5 | 0.0 | 0.000000 | 2779.0 |
| 11 | I | 40.3 | 69.0 | 148.5 | 1.004647 | 3028.0 |
| 12 | I | 36.8 | 142.5 | 60.0 | 0.980520 | 2592.5 |
| 13 | I | 46.9 | 96.0 | 129.0 | 1.005690 | 2808.0 |
| 14 | I | 34.1 | 79.5 | 88.0 | 0.987837 | 3689.5 |
| 15 | I | 41.6 | 134.0 | 111.0 | 0.996939 | 2367.0 |
| 16 | I | 38.4 | 141.0 | 49.5 | 0.498743 | 2245.0 |
| 17 | I | 39.8 | 141.0 | 21.0 | 0.477337 | 2964.5 |
| 18 | I | 33.3 | 141.0 | 11.0 | 0.433737 | 2621.5 |
| 19 | I | 37.6 | 176.5 | 0.0 | 0.000000 | 1485.5 |
| 20 | I | 39.2 | 112.5 | 60.0 | 0.960475 | 3209.0 |
| 21 | I | 31.6 | 141.0 | 33.5 | 0.466365 | 3575.0 |
| 22 | I | 47.2 | 83.0 | 72.0 | 0.497853 | 2762.0 |
| 23 | I | 28.8 | 141.0 | 78.0 | 0.942515 | 4217.5 |
| 24 | I | 33.2 | 141.5 | 12.5 | 0.532469 | 3131.5 |
| 25 | I | 34.8 | 140.0 | 0.0 | 0.000000 | 3091.0 |
| 26 | I | 31.0 | 127.5 | 33.5 | 0.509747 | 3750.0 |
| 27 | I | 36.4 | 141.5 | 0.0 | 0.000000 | 1969.5 |
| 28 | I | 31.8 | 143.0 | 0.0 | 0.000000 | 3365.5 |
| 29 | I | 35.2 | 135.5 | 11.0 | 0.526467 | 2707.5 |
| 30 | I | 37.4 | 142.5 | 0.0 | 0.000000 | 3110.5 |
| 31 | I | 34.8 | 141.0 | 73.0 | 0.946749 | 2546.0 |
| 32 | I | 38.3 | 147.5 | 1.5 | 0.466518 | 2146.5 |
| 33 | I | 42.8 | 116.0 | 43.0 | 0.495946 | 2168.0 |
| 34 | I | 37.0 | 139.5 | 0.0 | 0.000000 | 2564.5 |
| 35 | II | 13.6 | 77.0 | 175.0 | 1.143653 | 6142.0 |
| 36 | II | 25.8 | 50.5 | 92.0 | 0.511488 | 5429.5 |
| 37 | II | 26.7 | 69.5 | 252.0 | 1.084242 | 6088.5 |
| 38 | II | 27.1 | 81.0 | 184.5 | 0.981731 | 4651.0 |
| 39 | II | 18.8 | 129.0 | 165.0 | 1.000487 | 4661.5 |
| 40 | II | 22.6 | 144.0 | 91.0 | 0.949923 | 4093.5 |
| 41 | II | 29.4 | 114.5 | 193.0 | 0.981295 | 4267.5 |
| 42 | II | 25.0 | 188.0 | 59.0 | 0.912828 | 3682.5 |
| 43 | II | 23.5 | 125.0 | 75.0 | 1.107461 | 3970.0 |
| 44 | II | 23.8 | 105.5 | 175.0 | 0.993969 | 4657.0 |
| 45 | II | 22.0 | 119.5 | 122.0 | 0.988196 | 4882.0 |
| 46 | II | 20.9 | 137.0 | 147.0 | 0.981062 | 5119.0 |
| 47 | III | 12.9 | 112.5 | 173.0 | 1.032216 | 6197.5 |
| 48 | III | 14.0 | 73.5 | 279.0 | 1.010374 | 6777.5 |
| 49 | III | 19.6 | 32.0 | 202.5 | 1.033036 | 6506.0 |
| 50 | III | 12.2 | 158.5 | 161.5 | 0.953172 | 5204.5 |
| 51 | III | 22.1 | 58.0 | 240.5 | 1.026265 | 6476.5 |
| 52 | III | 18.8 | 123.5 | 102.0 | 0.967089 | 4643.0 |
| 53 | III | 16.4 | 118.5 | 168.0 | 0.993171 | 5953.5 |
| 54 | III | 19.9 | 150.0 | 40.5 | 0.828806 | 3923.5 |
| 55 | III | 13.0 | 139.5 | 153.0 | 0.923392 | 4858.0 |
| 56 | III | 18.4 | 143.0 | 138.0 | 0.997325 | 5414.5 |
| 57 | III | 14.1 | 142.0 | 188.5 | 0.982470 | 5031.5 |
| 58 | III | 17.8 | 114.5 | 157.5 | 1.013982 | 5157.5 |
| 59 | III | 16.8 | 141.0 | 109.0 | 0.930251 | 4767.5 |
| 60 | III | 16.5 | 121.0 | 77.5 | 0.995160 | 5509.0 |
| 61 | III | 19.2 | 121.0 | 107.0 | 1.000701 | 4354.5 |
| 62 | III | 15.9 | 121.0 | 227.0 | 1.038783 | 5744.0 |
| 63 | III | 19.7 | 104.5 | 181.5 | 0.946312 | 5074.5 |

Figure 29

OSTEOPOROSIS DIAGNOSTIC SUPPORT APPARATUS

RELATED APPLICATIONS

This application is a continuation-in-part application of, and claims priority to, PCT application number PCT/JP2014/081056 filed Nov. 25, 2014 (International Publication number WO2015/076406), which claims priority to JP2013-242678 filed Nov. 25, 2013, all of which are hereby incorporated by reference.

TECHNICAL FIELD

The present invention relates to an apparatus which supports osteoporotic diagnosis using X-ray photographs, and more particularly, to an apparatus which supports osteoporotic diagnosis by measuring a thickness, a coarseness, and/or a morphological index of the mandibular cortical bone using a dental panoramic X-ray photograph (hereinafter abbreviated to a panoramic image).

BACKGROUND ART

In the field of dental treatment, it is a widespread practice to shoot a panoramic image covering an entire area of a tooth portion at the start of treatment. In so doing, not only the tooth portion, but also the upper and lower jawbones are photographed. In recent years, of the shot images, images of a lower jawbone portion have come to be used to support osteoporotic diagnosis.

For example, Patent Literature 1 discloses a technical idea of supporting osteoporotic diagnosis by semiautomatically determining from a dental panoramic image whether an inner surface of a cortical bone portion of the lower jawbone is structured smoothly or coarsely.

Also, Patent Literature 2 discloses a technical idea of supporting osteoporotic diagnosis by measuring a thickness of a cortical bone portion of the lower jawbone from a dental panoramic image and comparing the thickness of the cortical bone with data accumulated in an osteoporosis database.

Also, Patent Literature 3 discloses a technical idea of supporting osteoporotic diagnosis by detecting a mandibular contour in a dental panoramic image and comparing a thickness of the mandibular cortical bone, in particular, with stored contour model data.

Furthermore, Non Patent Literature 1 discloses a technique for automatically measuring a thickness of the mandibular cortical bone using a dental panoramic image, and more particularly, a technical idea of acquiring a gray value profile of perpendicular lines from a mandibular contour and measuring the thickness of the mandibular cortical bone based on the mandibular contour.

Also, Patent Literature 4 discloses a technical idea of supporting osteoporotic diagnosis by automatically identifying an area where there is a change in bone density using a dental panoramic X-ray image.

CITATION LIST

Patent Literature

Patent Literature 1: Japanese Patent No. 3964795
Patent Literature 2: Japanese Patent No. 4956745
Patent Literature 3: International Publication No. 2012/128121
Patent Literature 3: Japanese Patent Laid-Open No. 2013-116293

Non Patent Literature

Non Patent Literature 1: Takuya Matsumoto, et al. "Osteoporosis screening by use of automated scheme for measuring mandibular cortical thickness on dental panoramic radiographs," The Institute of Electronics, Information and Communication Engineers, 2012-01
Non Patent Literature 2: Yukiyasu Yoshinaga, et al. "Evaluation Method of Concentration Degree and Convergence Index Filter," MEDICAL IMAGING TECHNOLOGY, Vol. 19, No. 3, May 2001, issued by The Japanese Society of Medical Imaging Technology. All of the above patent and non-patent literature are incorporated herein by reference in their entirety.

SUMMARY OF INVENTION

Technical Problem

However, a diagnostic support method of Patent Literature 1 has problems in that the method has insufficient measurement accuracy and complicated measuring means.

Also, a diagnostic support method of Patent Literature 2 has problems in that means of establishing outer and inner edges of the mandibular cortical bone is complicated and is low in accuracy.

Note that further improvement in accuracy is expected also from methods of Patent Literature 3 and Non Patent Literature 1 if there is a coarsely structured portion when the thickness of the mandibular cortical bone is measured.

Furthermore, the automatic osteoporosis diagnostic support method of Patent Literature 4 has problems in that it is difficult to use images shot by different apparatus, making it necessary to determine whether or not osteoporosis is suspected only by using images shot by a same apparatus and that it is not possible to automatically identify an osteoporotic morphological index (type I, type II, or type III) effective in making an osteoporotic diagnosis and classify symptoms or quantitatively show suspicion of osteoporosis.

Thus, to solve the above problems, an object of the present invention is to provide an apparatus which supports osteoporotic diagnosis by measuring a thickness, a coarseness, and/or a morphological index of the mandibular cortical bone using a dental panoramic image, wherein the apparatus can more accurately support osteoporotic diagnosis by more accurately measuring the thickness, coarseness, and/or morphological index of the mandibular cortical bone.

Solution to Problem

To achieve the above object, the present invention provides an osteoporosis diagnostic support apparatus comprising:
 a contour extraction unit adapted to extract a mandibular contour from an image of a mandibular cortical bone photographed by a photographic apparatus adapted to photograph the mandibular cortical bone and surroundings thereof;
 a line segment extraction unit adapted to extract line segments from the image of the mandibular cortical bone photographed by the photographic apparatus; and
 a cortical bone condition calculation unit adapted to calculate a condition of the cortical bone based on the extracted mandibular contour and line segments.

According to one aspect, in the osteoporosis diagnostic support apparatus with the above configuration, the cortical bone condition calculation unit may be a cortical bone thickness calculation unit adapted to calculate a thickness of the cortical bone.

Furthermore, according to an aspect of the present invention, the cortical bone thickness calculation unit may be configured to calculate the thickness of the cortical bone based on the line segments of the cortical bone extracted by the line segment extraction unit.

In particular, according to an aspect of the present invention, in the osteoporosis diagnostic support apparatus with the above configuration, the cortical bone thickness calculation unit may be configured to calculate the thickness of the cortical bone based on the line segments of the cortical bone extracted by the line segment extraction unit.

Consequently, if position which satisfies a predetermined condition within a range of a predetermined distance from the extracted line segments are established as an inner edge of the cortical bone, the thickness of the cortical bone can be measured accurately by eliminating the influence of noise and the like, which helps greatly in providing support for osteoporotic diagnosis.

Furthermore, according to an aspect of the present invention, in the osteoporosis diagnostic support apparatus with the above configuration, the cortical bone thickness calculation unit may be configured to calculate the thickness of the cortical bone based on the line segments of the cortical bone and line segments of a coarsely structured portion extracted by the line segment extraction unit.

Consequently, even if there are line segments in the coarsely structured portion, the inner edge of the cortical bone can be established accurately and the thickness of the cortical bone can be measured with high accuracy.

Alternatively, according to an aspect of the present invention, in the osteoporosis diagnostic support apparatus with the above configuration, the cortical bone condition calculation unit may be a cortical bone coarseness calculation unit adapted to calculate a coarseness of the cortical bone.

Furthermore, according to an aspect of the present invention, in the osteoporosis diagnostic support apparatus with the above configuration, the cortical bone coarseness calculation unit may be configured to calculate a coarseness of the cortical bone based on the line segments of the coarsely structured portion extracted by the line segment extraction unit.

This allows osteoporotic diagnosis to be supported easily due to largeness of the number or area of the extracted line segments in the coarsely structured portion.

Also, according to an aspect of the present invention, in the osteoporosis diagnostic support apparatus with the above configuration, a line-convergence index filter is used as the line segment extraction unit. This allows the line segments to be extracted easily and accurately.

Also, according to an aspect of the present invention, in the osteoporosis diagnostic support apparatus with the above configuration, determination of a measurement reference point in the cortical bone condition calculation unit includes detecting a mandibular angle. This allows the measurement reference point to be determined accurately by a simple and easy method.

Note that according to another aspect, the present invention may be implemented as an osteoporosis diagnostic support program configured to make a computer function as:
  contour extraction means for extracting a mandibular contour from an image of a mandibular cortical bone photographed by a photographic apparatus adapted to photograph the mandibular cortical bone and surroundings thereof;
  line segment extraction means for extracting line segments from the image of the mandibular cortical bone photographed by the photographic apparatus; and
  cortical bone condition calculation means for calculating a condition of the cortical bone based on the extracted mandibular contour and line segments, where the contour extraction means, the line segment extraction means, and the cortical bone condition calculation means correspond to the contour extraction unit, the line segment extraction unit, and the cortical bone condition calculation unit in the above description, respectively.

This allows the present invention to be implemented by a program regardless of the configuration of the apparatus.

Likewise, according to another aspect, the present invention may be implemented as an osteoporosis diagnostic support program configured to make a computer function as cortical bone thickness calculation means and cortical bone coarseness calculation means, which correspond, respectively, to the cortical bone thickness calculation unit and the cortical bone coarseness calculation unit in the above description.

Also, according to another aspect of the present invention, there is provided an osteoporosis diagnostic support apparatus comprising: a contour extraction unit adapted to extract a mandibular contour from an image of a mandibular cortical bone photographed by a photographic apparatus adapted to photograph the mandibular cortical bone and surroundings thereof; a line segment extraction unit adapted to extract line segments from the image of the mandibular cortical bone photographed by the photographic apparatus, where the line segments are formed by a gray level distribution and include line segments of the cortical bone and line segments of a coarsely structured portion; and a mandibular cortical bone morphological index identification unit adapted to extract a feature value based on at least one of the extracted mandibular contour and line segments and identify a mandibular cortical bone morphological index by the feature value.

This makes it possible to identify type I to type III below, which belongs to the morphological index of the mandibular cortical bone for use to support osteoporotic diagnosis. Type I is characterized by smooth inside surfaces of the cortical bone on both sides, Type II is characterized by irregular inside surfaces of the cortical bone and in that linear absorption is observed in a neighborhood of an inner side inside the cortical bone, and Type III is characterized in that advanced linear absorption as well as fractures of the cortical bone are observed over the entire cortical bone.

The feature value may include one or more of:
  a feature value of the thickness of the cortical bone,
  the number of pixels of line elements in a cortical bone region estimated to be dense when regions classified by density are estimated based on the extracted mandibular contour and line segments,
  the number of pixels of line elements in a cortical bone region estimated to be coarse in the estimation of the regions classified by density,
  area of the cortical bone region estimated to be coarse in the estimation of the regions classified by density,
  a ratio of average concentration value of line elements between the cortical bone region estimated to be dense and the cortical bone region estimated to be coarse in the estimation of the regions classified by density, 0-, 45-, 90-, or 135-degree variance of the cortical bone region estimated to be coarse in the estimation of the regions classified by density, 0-, 45-, 90-, or 135-degree difference variance of the cortical bone region estimated to be coarse in the estimation of the regions classified by density, 45-, 90-, or 135-degree difference entropy of the cortical bone region estimated to be coarse in the estimation of the regions classified by density, 0-degree inverse difference moment of all cortical bone regions estimated to be dense or coarse in the estimation of the regions classified by density, 0-degree difference entropy of all the cortical bone regions estimated to be dense or coarse in the estimation of the regions classified by density, and 0-degree difference variance of all the cortical bone regions estimated to be dense or coarse in the estimation of the regions classified by density.

Consequently, feature values useful in providing support for osteoporotic diagnosis are used selectively or in combination, a morphological index can be found with high accuracy.

Note that the mandibular cortical bone morphological index identification unit may be an identification unit made up of a support vector machine. This enables efficient identification even when a large number of feature values are used for identification.

Furthermore, the mandibular cortical bone morphological index identification unit may have a bone density estimation function. Use of the feature values described so far makes it possible to quantitatively estimate bone density and thereby support appropriate osteoporotic diagnosis.

Note that according to another aspect, the present invention may be implemented as an osteoporosis diagnostic support program configured to make a computer function as:

contour extraction means for extracting a mandibular contour from an image of a mandibular cortical bone photographed by a photographic apparatus adapted to photograph the mandibular cortical bone and surroundings thereof;

line segment extraction means for extracting line segments from the image of the mandibular cortical bone photographed by the photographic apparatus; and a mandibular cortical bone morphological index identification means for extracting a feature value based on at least one of the extracted mandibular contour and line segments and identifying a mandibular cortical bone morphological index by the feature value, where the contour extraction means, the line segment extraction means, and the mandibular cortical bone morphological index identification means, which correspond, respectively, to the contour extraction unit, line segment extraction unit, and the mandibular cortical bone morphological index identification unit in the above description.

This allows the present invention to be implemented by a program regardless of the configuration of the apparatus.

Advantageous Effects of Invention

The osteoporosis diagnostic support apparatus according to the present invention obtains information useful for osteoporotic diagnosis from images of the mandibular cortical bone and achieves great effects in diagnostic support. In particular, the aspect of the invention described above can accurately calculate a cortical bone thickness regardless of the presence or absence of a coarsely structured portion, or quantitatively calculate a coarseness of coarsely structured portions, making it easy to support osteoporotic diagnosis. Also, another aspect of the invention, makes it possible to obtain the osteoporotic morphological index (type I, type II, or type III) useful in supporting osteoporotic diagnosis, which helps in providing support for osteoporotic diagnosis.

BRIEF DESCRIPTION OF DRAWINGS

FIG. 6 is an explanatory diagram of profile acquisition on the osteoporosis diagnostic support apparatus according to the first embodiment of the present invention.

FIGS. 7A to 7C are images created using profiles of the osteoporosis diagnostic support apparatus according to the first embodiment of the present invention.

FIGS. 18A and 18B are images obtained before and after application of a line-convergence index filter of the osteoporosis diagnostic support apparatus according to the first embodiment of the present invention.

FIGS. 19A and 19B are result images of the osteoporosis diagnostic support apparatus according to the first embodiment of the present invention.

FIG. 29 is an explanatory diagram of cases on the osteoporosis diagnostic support apparatus according to the second embodiment of the present invention.

DESCRIPTION OF EMBODIMENTS

An osteoporosis diagnostic support apparatus according to a first embodiment of the present invention is described below with reference to the drawings. Note that description is given below schematically to the extent necessary to achieve the object of the present invention, that description is given mainly to the extent necessary to describe appropriate parts of the present invention, and that description related to known techniques is omitted.

Figure 1:
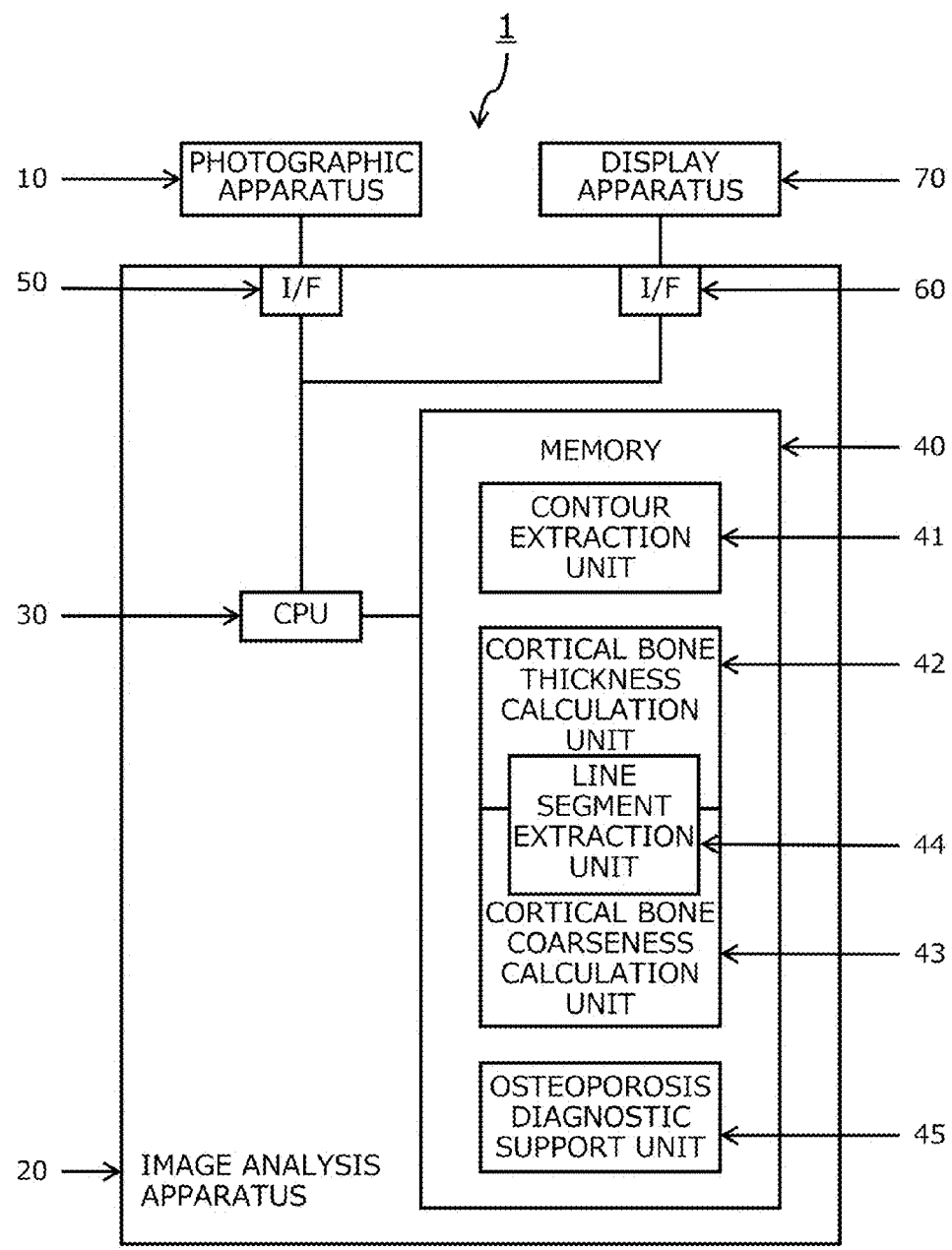
FIG. 1 is a block diagram of an osteoporosis diagnostic support apparatus according to a first embodiment of the present invention.

FIG. 1 is a block diagram of the osteoporosis diagnostic support apparatus according to the first embodiment of the present invention. As shown in FIG. 1, the osteoporosis diagnostic support apparatus 1 includes a photographic apparatus 10 adapted to shoot subject images of patients or the like, an image analysis apparatus 20 adapted to analyze images shot by the photographic apparatus 10, and a display apparatus 70 adapted to display the images shot by the photographic apparatus 10 and information obtained by the image analysis apparatus 20, where these apparatus are linked together by wired and/or wireless connections.

The image analysis apparatus 20 includes a CPU 30, a memory 40, and interfaces 50 and 60, which are linked, for example, as shown in FIG. 1. The memory 40 includes a contour extraction unit 41, a cortical bone thickness calculation unit 42, a cortical bone coarseness calculation unit 43, a line segment extraction unit 44, and an osteoporosis diagnostic support unit 45.

A panoramic X-ray imaging apparatus, which is a type of the photographic apparatus 10, is an apparatus adapted to shoot panoramic images in the dental area with X-rays. Various types of panoramic X-ray imaging apparatus have been put to practical use and any of them may be adopted. Note that the photographic apparatus 10 is not limited to the panoramic X-ray imaging apparatus, and any of a usual X-ray imaging apparatus, MRI/CT imaging apparatus, ultrasound imaging apparatus, or a combination thereof may be adopted as the photographic apparatus 10. Appropriate diagnostic support may be provided by resulting images.

The panoramic image shot by the panoramic X-ray imaging apparatus serving as the photographic apparatus 10 is sent to the image analysis apparatus 20. The image analysis apparatus 20 analyzes images, being provided with computer resources including at least the CPU 30, memory 40, interface 50 with the photographic apparatus 10, and interface 60 with the display apparatus 70 (described later). The computer resources may be provided in the form of a server or personal computer installed in close proximity, similar apparatus linked by wired and/or wireless connections, or Internet-based cloud.

The display apparatus 70 is connected to the image analysis apparatus 20 via the interface 60 and is capable of displaying the images shot by the photographic apparatus 10, images of a mandibular contour and line segments extracted by the image analysis apparatus 20, information about a thickness, a coarseness, and the like of the cortical bone calculated by the image analysis apparatus 20, osteoporosis diagnostic support information obtained by the image analysis apparatus 20, and the like.

The contour extraction unit 41 is provided as a program stored in the memory 40 of the image analysis apparatus 20. The contour extraction unit 41 extracts a mandibular contour from a panoramic image. The mandibular contour is a portion which defines an outer edge of the lower jawbone.

Also, the cortical bone thickness calculation unit 42, which is one of cortical bone condition calculation units, is provided as part of the image analysis apparatus 20. The cortical bone thickness calculation unit 42 is a program stored in the memory, and is capable of causing a computer to perform a function to calculate a thickness of the cortical bone from a panoramic image.

Furthermore, the cortical bone coarseness calculation unit 43, which is one of the cortical bone condition calculation units, is provided as part of the image analysis apparatus 20. The cortical bone coarseness calculation unit 43 is a program stored in the memory, and is capable of causing a computer to perform a function to calculate a coarseness of the cortical bone from a panoramic image.

Besides, the line segment extraction unit 44 is provided as part of the image analysis apparatus 20. The line segment extraction unit 44, which is, for example, like a line-convergence index filter, is a program stored in the memory, and is capable of causing a computer to perform a function to extract line segments from a panoramic image. The line segment extraction unit 44 is used as part of the cortical bone thickness calculation unit 42 and also as part of the cortical bone coarseness calculation unit 43.

Note that any one or both of the cortical bone thickness calculation unit 42 and cortical bone coarseness calculation unit 43 may be provided.

Furthermore, the osteoporosis diagnostic support unit 45 is provided as part of the image analysis apparatus 20, allowing calculation results produced by the cortical bone thickness calculation unit 42 and cortical bone coarseness calculation unit 43 to be compared with the data stored in an osteoporosis diagnostic support database (not shown), which is part of the osteoporosis diagnostic support unit 45.

Figure 2:
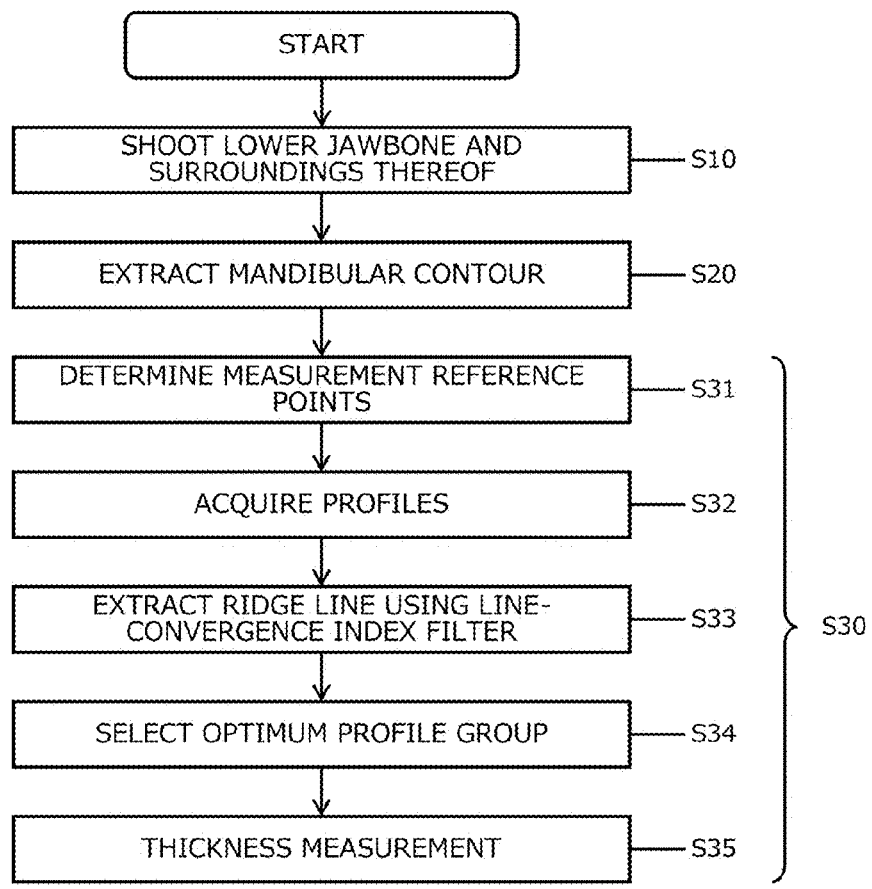
FIG. 2 is a flowchart of the osteoporosis diagnostic support apparatus according to the first embodiment of the present invention.

Now, operation of the osteoporosis diagnostic support apparatus configured as described above is described. FIG. 2 is a flowchart of the osteoporosis diagnostic support apparatus according to the first embodiment of the present invention.

<Image Shooting> (S10)

First, images of the lower jawbone and surroundings thereof are shot by a panoramic X-ray imaging apparatus, which is a type of the photographic apparatus 10.

<Contour Extraction> (S20)

Next, the shot dental panoramic image is inputted to the image analysis apparatus 20, and the mandibular contour is extracted by the contour extraction unit 41, which is part of the image analysis apparatus 20.

Specifically, this is done as follows. First, edges are detected in the image by Canny method. This is done by performing a) image smoothing, b) calculation of edge strength and direction, c) non-maximum suppression, and d) hysteresis thresholding in this order, and Kirsch's method which is a template edge detection operator is used in conjunction to inhibit detection of edges irrelevant to the lower jawbone.

Figure 3:
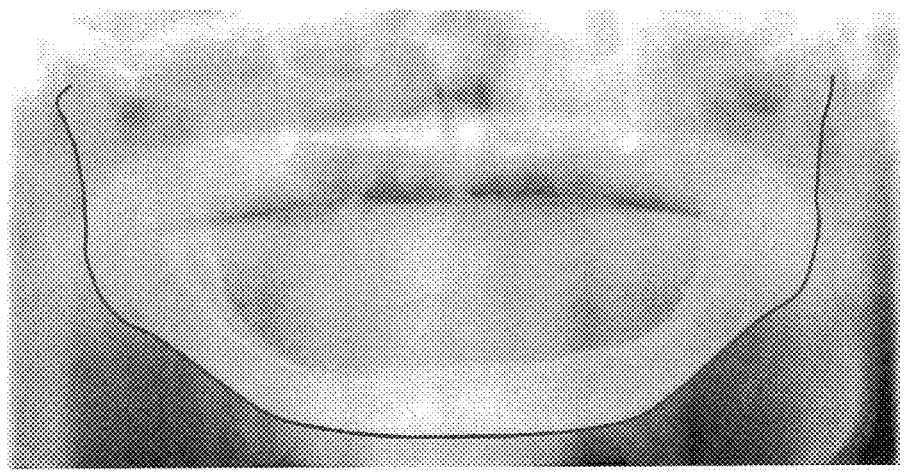
FIG. 3 is an example of an image obtained when a result of extracting a mandibular contour by the osteoporosis diagnostic support apparatus according to the first embodiment of the present invention is displayed in overlays on a panoramic image.

Furthermore, to extract a mandibular contour as a more accurate line from the image subjected to edge extraction, a dynamic contour model method is used. The techniques mentioned so far are described in detail in Patent Literature 3. FIG. 3 is an example of an image obtained when a result of extracting a mandibular contour using these techniques is displayed in overlays on a panoramic image.

Next, description will be given of detailed operation of the cortical bone thickness calculation unit 42 which calculates a cortical bone thickness using the shot image and extracted contour. As shown in FIG. 2, the cortical bone thickness calculation unit 42 (related to step S30) includes a function to implement the following steps.

<Determination of Measurement Reference Points> (S31)
<Acquisition of Profiles> (S32)
<Ridge Line Extraction Using Line-Convergence Index Filter> (S33)
<Profile Group Selection> (S34)
<Thickness Measurement> (S35)

These steps are described in detail below. Note that the numeric values cited in the description are desirable examples, but are not restrictive, and that numeric values may be selected, as appropriate, according to conditions of the image or accuracy of diagnostic support.

<Determination of Measurement Reference Points>

Measurement reference points are found from a mandibular contour. To calculate a state (thickness or coarseness) of the lower jawbone, it is desirable to establish measurement reference points near locations immediately under the foramen mentale on both right and left sides, which enable stable calculations.

Figure 4:
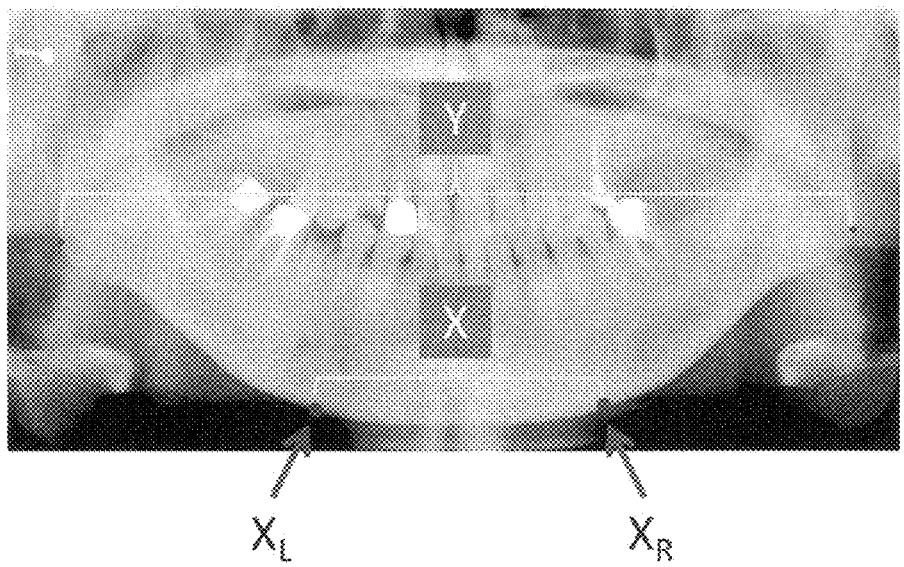
FIG. 4 is an explanatory diagram of measurement reference points on the osteoporosis diagnostic support apparatus according to the first embodiment of the present invention.

FIG. 4 is an explanatory diagram of measurement reference points. Specifically, measurement reference points $X_L$ and $X_R$ on both sides are found using the following technique.

a) Detect mandibular angles. The mandibular angles, which exist on both right and left sides, correspond to spots at which angles formed by tangents to the mandibular contour and a perpendicular line become 15 degrees or less for the first time.

b) A distance obtained by multiplying a distance Y between the right and left mandibular angles by a predetermined coefficient is established as a distance between the right and left measurement reference points. Preferably the predetermined coefficient for positions corresponding to the foramen mentale is set to 0.48 based on data accumulated so far, but this is not restrictive.

c) The distance between the measurement reference points is divided at the central part of the mandibular contour into right and left, and the two measurement reference points are denoted by $X_L$ and $X_R$.

Now, although it has been stated that the spots at which angles formed by tangents to the mandibular contour and a perpendicular line become 15 degrees or less for the first time are used in detecting the mandibular angles, the angle used in detecting the mandibular angles is not limited to 15 degrees or less, and may be 20 degrees or less. Also, it is not necessary to detect the mandibular angles exactly, and spots close to the mandibular angles and effective in determining measurement reference points may be used. Even in that case, the angle is not limited to 15 degrees, and may be larger (e.g., 25 degrees) or smaller (e.g., 10 degrees).

Note that the method for determining measurement reference points is not limited to the above method, and may be a method which involves detecting the foramen mentale by enhancing light and shade such as described in Patent Literature 1 or a method which involves determining measurement reference points in comparison with a contour model database which records positions corresponding to the foramen mentale such as described in Patent Literature 3.

<Acquisition of Profiles>

Next, plural points are established at predetermined intervals around each measurement reference point on the mandibular contour, a perpendicular line from each of the points to the mandibular contour is acquired, and gray values are found at predetermined intervals on the perpendicular line. Changes in the gray values are represented by what is known as a profile.

Figure 5:
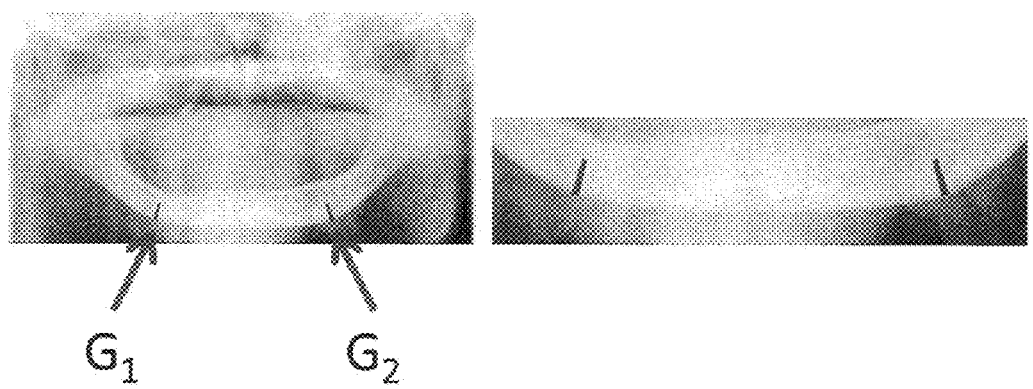
FIG. 5 is an explanatory diagram of image creation on the osteoporosis diagnostic support apparatus according to the first embodiment of the present invention.

Specifically, as shown in the explanatory diagram of image creation in FIG. 5, images $G_1$ and $G_2$ 101 pixels wide along the mandibular contour and 100 pixels long in a vertical direction from the mandibular contour are created, respectively, around the right and left measurement reference points, where 1 pixel=0.1 mm.

The profile is acquired as follows. FIG. 6 is an explanatory diagram of profile acquisition.

First, a Gaussian filter is applied to the profile to remove noise from the profile. The Gaussian filter is given by the following Equation.

$$f(x) = \frac{1}{\sqrt{2\pi}\,\sigma} \exp\left(-\frac{x^2}{2\sigma^2}\right) \qquad \text{[Mathematical expression 1]}$$

The smaller the value of σ, the smaller the effect of smoothing while the larger the value, the larger the effect. Here, it is assumed that σ=0.8, but the value may be changed according to image quality.

Note that the noise removal filter is not limited to the Gaussian filter, and various filters are conceivable, including a moving average method, a median filter, a bilateral filter, an anisotropic diffusion filter, and a non-local means filter depending on the situation, any of which may be applied.

Subsequent procedures are as follows.

a) Pixel values are determined on a total of 101 perpendicular lines from the right and left measurement reference points and 100 points therearound on the mandibular contour and converted into images. That is, an image is created as follows: the $x_i$th point from the left side of the contour out of the points on the contour used and a pixel value at a distance $y_i$ ($y_i$=1 to 100) from a measurement start point determined from the profile are converted into a pixel value at coordinates ($x_i$, $y_i$) on an image created in advance. The lowermost end of the image created corresponds to the mandibular contour or the measurement start point of the profile.

b) Position of a peak on each of the acquired profiles is extracted, and the pixel values at locations corresponding to the image are maximized, i.e., turned white.

Here, in the example of FIG. 6, a lower left portion (b) of FIG. 6 shows the profile at the first point $X_{LL}$ from the left end as viewed from the measurement reference point $X_L$ on the observers' left on the mandibular contour, and it can be seen that gray value peeks exist at spots at distances of 28, 50, 61, 72, 89, and 98 pixels from the measurement start point.

Also, a lower right portion (c) of FIG. 6 shows an extracted peak of a profile. When relevance of the peak is observed in (c) portion of FIG. 6, it can be seen that gray value peeks of a coarse structure and the cortical bone desired to be extracted stretch continuously in a horizontal direction of the image. Using the continuity of peaks on plural profiles, gray value peeks on a coarse structure can be identified.

<Ridge Line Extraction Using Line-Convergence Index Filter>

Next, description will be given of a technique for applying a line-convergence index filter to an image created from a profile, to extract line segments (referred to as ridge lines) formed by a density distribution. Note that an outline of the technique is disclosed in Non Patent Literature 2.

Here, steps up to step a) described in relation to the profile acquisition are carried out. Note that no peak extraction is performed. That is, an image such as shown in each of FIGS. 7A to 7C is created as follows: the $x_i$th point from the left side of the contour out of the points on the contour used and a pixel value at a distance $y_i$ ($y_i$=1 to 100) from a measurement start point determined from the profile are converted into a pixel value at coordinates ($x_i$, $y_i$) on a created image. The lowermost end of the image created corresponds to the mandibular contour or the measurement start point of the profile.

Then, to extract ridge lines (places where gray value peeks stretch continuously), a line-convergence index filter is applied to the image created using a profile.

Figure 8:
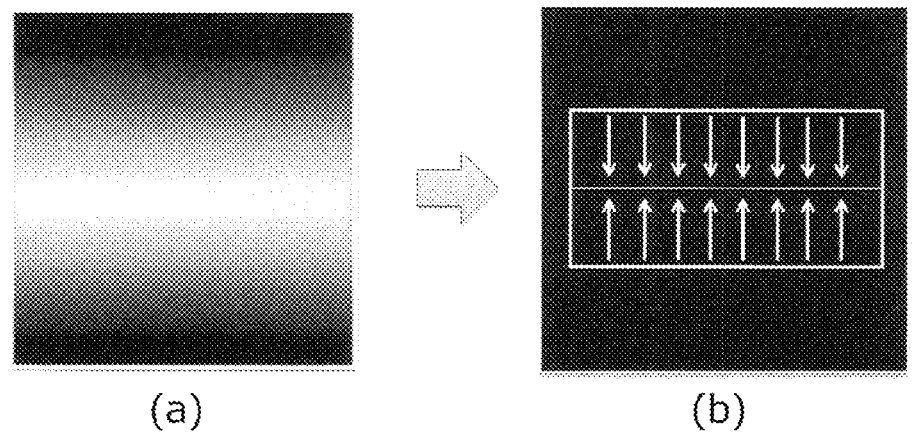
FIG. 8 is an explanatory diagram showing an outline of a line-convergence index filter of the osteoporosis diagnostic support apparatus according to the first embodiment of the present invention.

The line-convergence index filter is a line detection filter when a straight line is regarded as a target. FIG. 8 is an explanatory diagram showing outline of a line-convergence index filter used for this technique, where central portion is the brightest and a region such as shown in (a) portion of FIG. 8 in which isophotes extend in parallel corresponds to this, and the region is called a linear convex region. A distribution of the intensity gradient vectors whose directions all converge perpendicularly to a center line as shown in (b) portion of FIG. 8, is referred to as a line-convergence vector field and designated as a basic model. Also, the line on which the vectors converge is referred to as a vector-convergence line. Hereinafter, the degree of vector convergence on a line will be referred to as a line convergence index.

Figure 9:
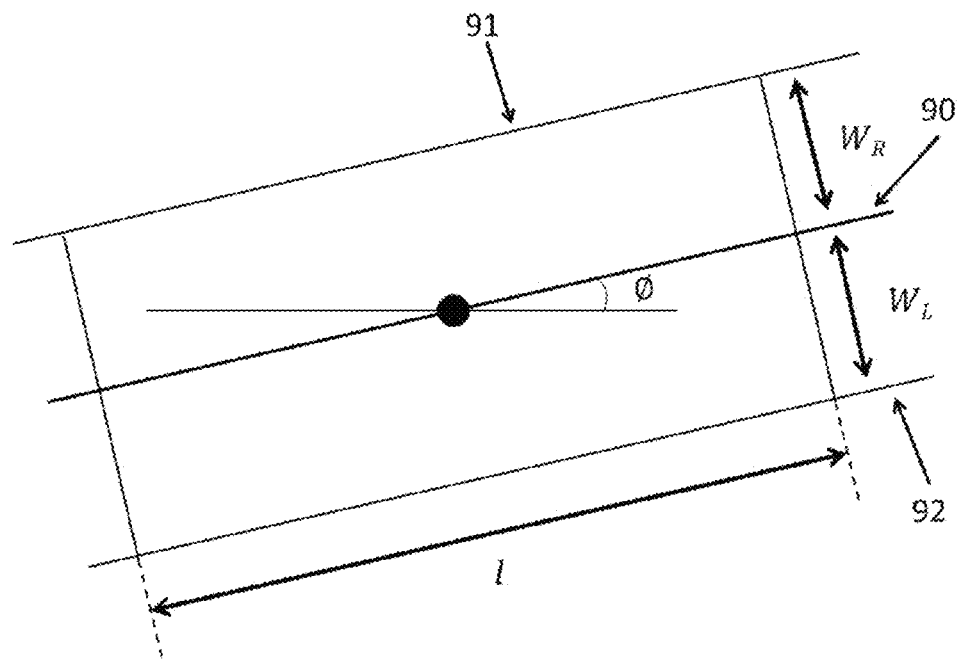
FIG. 9 is an explanatory diagram of search lines on the osteoporosis diagnostic support apparatus according to the first embodiment of the present invention.

FIG. 9 is an explanatory diagram of search lines used for this technique. A straight line 90 in a direction φ is considered, and assumed to be a vector-convergence line. A search line 91 and search line 92 parallel to the straight line are considered, and rectangular regions with a width of $W_R$ or $W_L$ and length of l are considered on both sides (R side and L side) of the straight line in a region enclosed by the search lines 91 and line 92. If $θ_{ij}$ (φ) is an angle formed by the intensity gradient vector of the jth pixel on a search line with a distance of i in the regions and a perpendicular line drawn therefrom to the vector-convergence line, an evaluation value $C_R$ on the R side can be defined as follows.

$$C_R(\phi) = \max_{0 < w_R \leq w_{max}} \frac{1}{lw_R} \sum_{i=1}^{w_R} \sum_{j=0}^{l} \cos(\theta_{ij}(\phi))$$ [Mathematical expression 2]

where Wmax is the largest search width. The same applies to an evaluation value $C_L$ on the L side. It is assumed that the line convergence index at a point of interest in the assumed direction φ is given by an average value of $C_R$ and $C_L$. Because an actual direction of the vector-convergence line is unknown, the range in FIG. 9 is divided according to the purpose, the convergence index in each direction is determined, and the largest value of the convergence index is designated as an output C of the line-convergence index filter. The line-convergence index filter is less susceptible to contrast with the background, and is adaptable to variation in line width as well. When the point of interest is located on the vector-convergence line, i.e., when luminance is placed on a third axis, output from the part corresponding to the ridge line takes a maximum value of 1. With increasing distance from the vector-convergence line, the output decreases monotonously, and takes 0.5 in a peripheral portion.

When the maximum search width Wmax is made very small, the output of the line-convergence index filter takes 1 on the vector-convergence line, but decreases rapidly with increasing distance from the vector-convergence line. Using this property, processes corresponding to thinning and ridge line extraction can be implemented.

The line-convergence index filter is used to extract ridge lines from an image created using profiles. Then, by making the maximum search width Wmax for ridge line extraction very small, parameters of the line-convergence index filter are set as follows.

Maximum search width: Wmax=3 [pix]
Width: R=8, L=8
Assumed directions: φ=0, 15, 30, 45, 135, 150, and 165 degrees These angles are preferable because the cortical bone and coarse structure have a vector-convergence line in the horizontal direction with respect to the lowermost end of the image (the lowermost end of the image corresponds to the mandibular contour).

Figure 10:
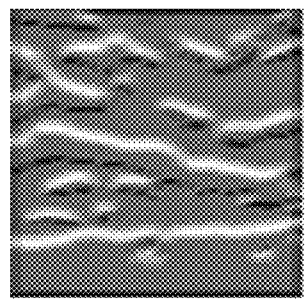
FIG. 10 is an image showing results of line-convergence index filtering on the osteoporosis diagnostic support apparatus according to the first embodiment of the present invention.

By setting the above-mentioned parameter, the line-convergence index filter is applied to the image of each of FIGS. 7A to 7C. FIG. 10 is an explanatory diagram showing results of line-convergence index filtering, and it can be seen that portions corresponding to the ridges in the image react strongly.

Figure 11:
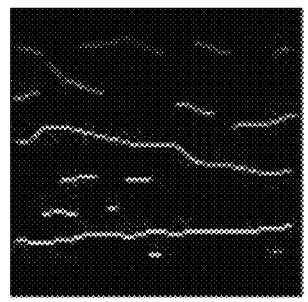
FIG. 11 is an image showing results of ridge line extraction on the osteoporosis diagnostic support apparatus according to the first embodiment of the present invention.

FIG. 11 is an explanatory diagram showing results of ridge line extraction. Furthermore, to extract ridges as lines, when the output C of the line-convergence index filter is 0.50 or less (i.e., $\theta_{ij}(\phi)$>45 degrees, where $\theta_{ij}(\phi)$ is an angle from the perpendicular line to the vector-convergence line), the output is assumed to be 0. Finally, lines to be ridge lines are extracted through thinning and very low-value thresholding.

<Selection of Ridge Lines>

It is assumed that the ridge lines extracted by the application of a line-convergence index filter are classified into three types: ridge lines formed by gray value peaks of the cortical bone, ridge lines formed by gray value peaks of coarse structure, and noise. The lines on the image subjected to ridge line extraction as shown in FIG. 11 are classified by the following method.

Note that for simplicity, "the ridge lines formed by gray value peaks of the cortical bone" will be referred to as "ridge lines of the cortical bone" while "the ridge lines formed by gray value peaks of coarse structure" will be referred to as "ridge lines of coarse structure."

a) Noise Removal

Any line less than 15 pixels in width along an x-axis is judged to be a noise and is deleted from the image. The value of 15 pixels is used because measurements are taken using 15 profiles in the end.

b) Ridge Line of Cortical Bone

After the noises are deleted, the line existing at the lowermost end of the image is designated as a ridge line of the cortical bone.

c) Ridge Line of Coarse Structure

It is estimated from sample data that a boundary between the cortical bone and cancellous bone in the profile exists at a spot between a gray value peak Ts and Ts+20 [pix]. Thus, in the image after noise deletion, any line located 20 pixels or more away from the line selected in b) along a y-axis is deleted as having no effect on thickness measurement.

Figure 12:
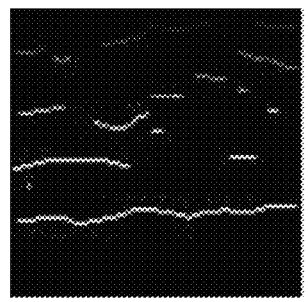
FIG. 12 is an image obtained before ridge line selection on the osteoporosis diagnostic support apparatus according to the first embodiment of the present invention.
Figure 12:
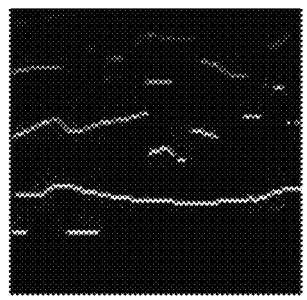
Figure 13:
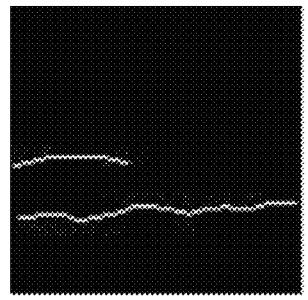
FIG. 13 is an image obtained after ridge line selection on the osteoporosis diagnostic support apparatus according to the first embodiment of the present invention.
Figure 13:
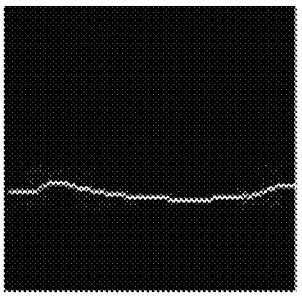

Also, to prevent large dispersion from occurring in thickness measurement values and credibility of thickness measurement from being lost, any line overlapping the line selected in b) at less than 15 coordinate points along the x-axis is deleted. The number of 15 is used because 15 profiles are used in thickness measurement in the end. Note that FIG. 12 and FIG. 13 are images before and after ridge line selection.

<Selection of Most Optimum Profile Group>

Figure 14:
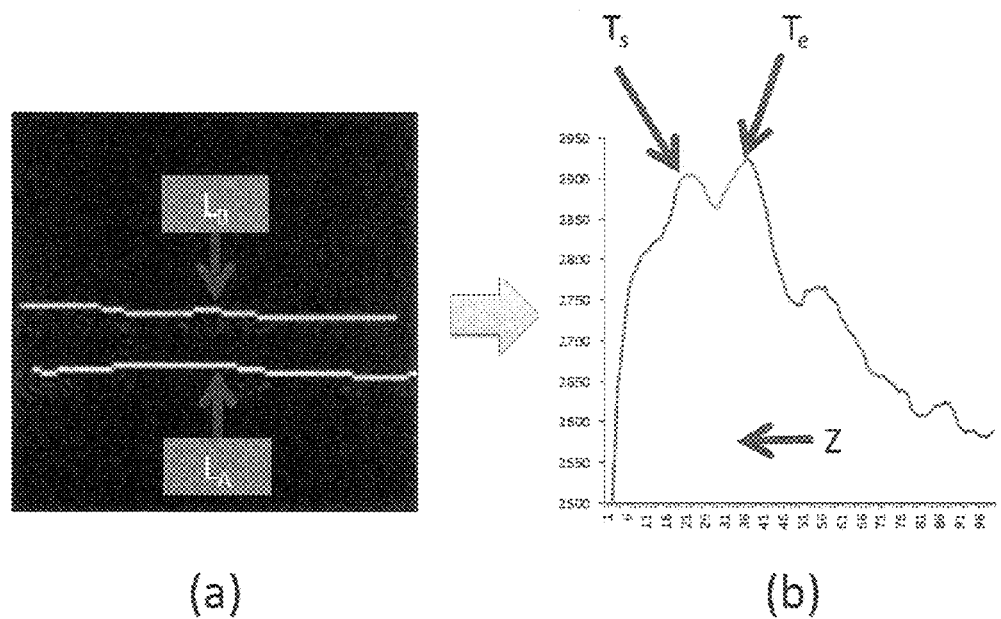
FIG. 14 is an explanatory diagram of an appropriate search range on the osteoporosis diagnostic support apparatus according to the first embodiment of the present invention.

Subsequently, a profile group considered to be most useful for thickness measurement of the mandibular cortical bone is selected. If there is a coarse structure in the cortical bone region whose thickness is measured, gray value peeks of the cortical bone and coarse structure can be selected from a large number of peaks existing in the acquired profiles using the ridge lines of the cortical bone and coarse structure extracted earlier. That is, as shown in the illustration of an appropriate search range in FIG. 14, the start point Ts and end point Te of a search range Z on the profile can be dynamically changed to an appropriate position on a profile by profile basis using the ridge line $L_A$ of the cortical bone and ridge line $L_B$ of the coarse structure, making it possible to measure the thickness with high accuracy. Note that in a right portion (b) of FIG. 14, the abscissa represents the distance [pix] from the measurement start point while the ordinate represents the gray value.

Furthermore, because the search range extends to the gray value peak of the coarse structure, a profile existing at a location where the boundary between the cortical bone and cancellous bone is clear can be selected.

Description will be given below of details of a method for dynamically determining a search range and a method for selecting a profile group best suited for the thickness of the mandibular cortical bone.

a) Using Only the Profile Containing an Extracted Ridge Line of the Cortical Bone When there is an x-axis without any ridge line of the cortical bone, it is considered that the gray value peak of the cortical bone is not formed stably in the profile corresponding to the x-axis, and thus the profile is not used because of unsuitability for thickness measurement of the cortical bone.

b) A Method for Determining a Search Range on a Profile by Profile Basis

Only the profile corresponding to an image containing an extracted ridge line of the cortical bone is used for thickness measurement. The method for determining a search range is determined as follows.

b-1) If the profile contains a spot corresponding to the ridge line of coarse structure, a search start point Ts and search end point Te are set at the gray value peak of the cortical bone and gray value peak of the coarse structure, respectively, using the determined ridge line.

b-2) If the profile does not contain any spot corresponding to the ridge line of coarse structure, the search start point Ts is set at the gray value peak of the cortical bone and the search end point Te is set at Ts+20 pixels, using the determined ridge line.

c) Selecting the Best Profiles.

To determine the 15 best adjacent profiles, candidates for the best profiles are narrowed down according to the presence or absence of a ridge line of coarse structure. Then, a technique for determining the 15 best adjacent profiles based on a decrease width of the search range is used. Details of the technique for selecting the best profiles are shown below.

c-1) Selecting Candidates for the Best Profiles According to the Presence or Absence of a Ridge Line of Coarse Structure When the image contains a ridge line of coarse structure, if a profile contains a peek corresponding to a ridge line attributable to a gray value peak of coarse structure, the profile is included in a candidate group for the best profiles and any profile without a peek is excluded from the candidates for the best profiles.

When the image does not contain a ridge line of coarse structure, all the profiles containing any extracted gray value peak of the cortical bone are adopted as candidates without narrowing down candidates for the best profiles.

Figure 15:
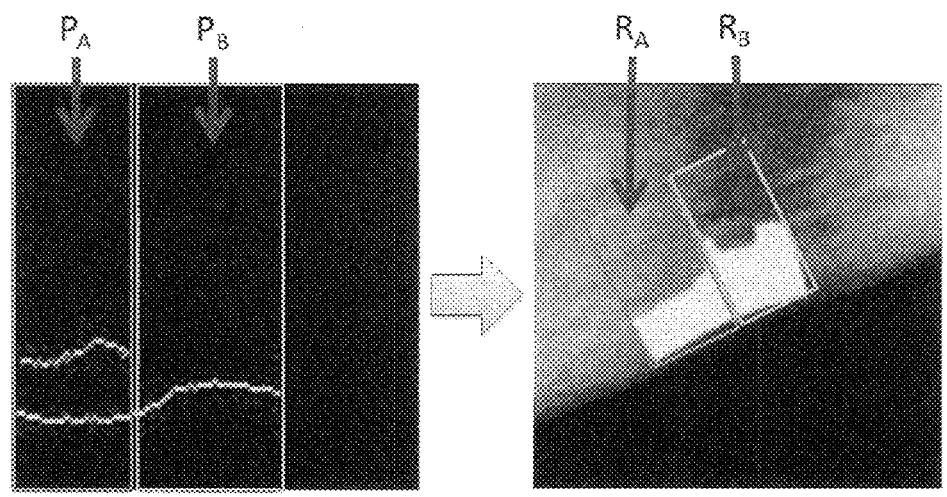
FIG. 15 is an explanatory diagram showing an effect of the presence or absence of a ridge line of coarse structure on measurement results of the osteoporosis diagnostic support apparatus according to the first embodiment of the present invention.
Figure 16A:
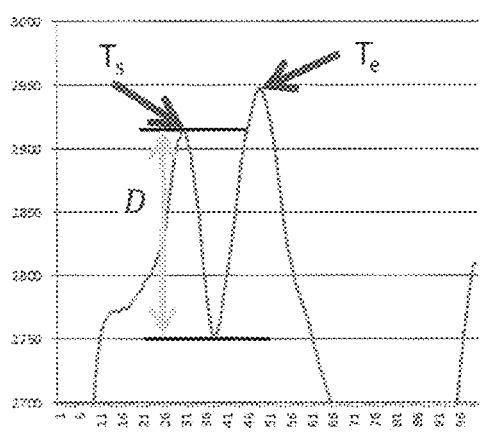
FIGS. 16A and 16B are explanatory diagrams showing a decrease width of gray value on the osteoporosis diagnostic support apparatus according to the first embodiment of the present invention.
Figure 16B:
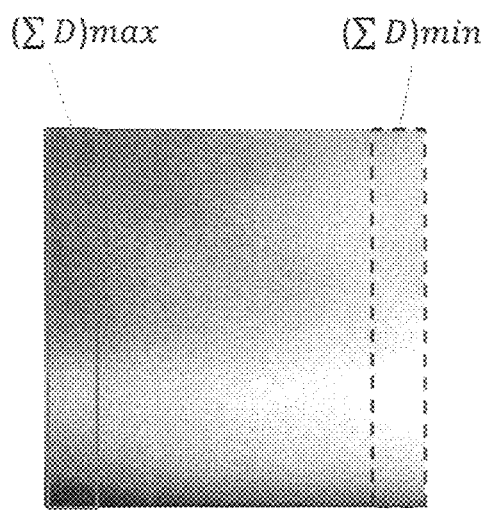

FIG. 15 is an explanatory diagram showing an effect of the presence or absence of a ridge line of coarse structure on measurement results. In thickness measurement, measurement results $R_A$ produced using a profile $P_A$ containing a ridge line of coarse structure are more stable than measurement results $R_B$ produced using a profile $P_B$ without any ridge line of coarse structure.

c-2) Determining the 15 Best Adjacent Profiles Using the Decrease Width of the Search Range Finally, the decrease width between the gray value at the search start point Ts and the smallest gray value in the search range is determined from the profile selected according to the procedures of "selecting candidates for the best profiles according to the presence or absence of a ridge line of coarse structure." FIGS. 16A and 16B are explanatory diagrams showing a decrease width of gray value, where the decrease width D between Ts and Te shown in FIG. 16A on the left represents clearness of the boundary between the cortical bone and cancellous bone as shown in FIG. 16B on the right and selecting a profile with a large decrease width is tantamount to selecting a profile suitable for thickness measurement of the cortical bone. Thus, subsequent to the procedures of "selecting candidates for the best profiles according to the presence or absence of a ridge line of coarse structure," a profile group which maximizes the sum total ΣD of decrease widths of 15 adjacent profiles is further selected, thereby implementing the selection of the best profiles.

<Measurement of Thickness of Cortical Bone>

Finally, thickness measurements are made using the selected profile group.

Using the 15 best adjacent profiles determined by the above technique as well as a dynamic search range, the boundary between the cortical bone and cancellous bone is set based on a gradient of the profile as described below, thereby measuring the thickness of the cortical bone.

The thickness measurement of the cortical bone based on the gradient of the profile involves determining the gradients ($A_1, A_2, \ldots, A_{15}$) of the profile at each of points beginning with a measurement start point and calculating an average Aave of only the gradients associated with decreasing gray values. Next, a point Tresult closest to Ts which satisfies the condition of Ai<Aave is determined, and the distance from the measurement start point to Tresult is designated as the thickness of the cortical bone.

The thickness of the cortical bone is displayed on the display apparatus 70, supporting a physician in making an osteoporotic diagnosis or is compared with data stored in the osteoporosis diagnostic support database, which is part of the osteoporosis diagnostic support unit 45, making it possible to judge the progress of osteoporosis and support osteoporotic diagnosis.

Figure 17:
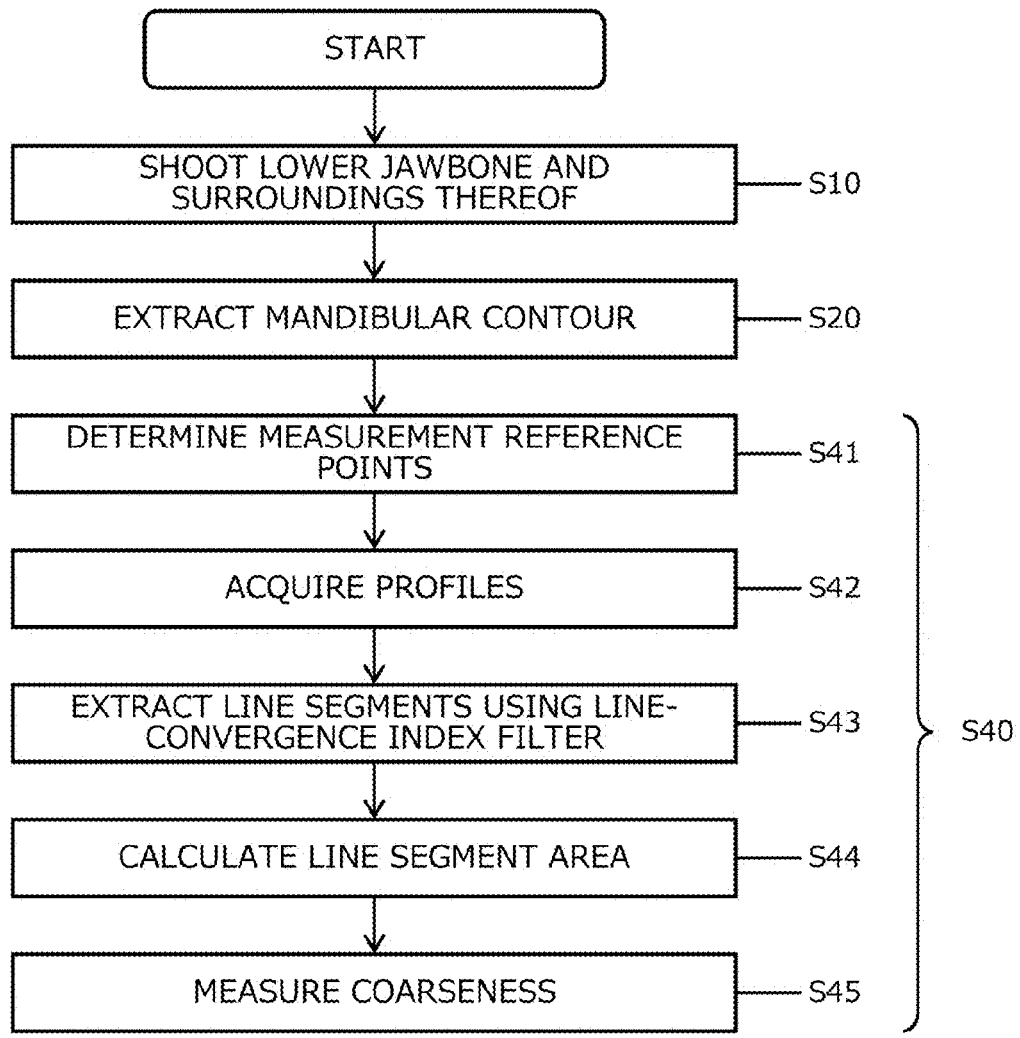
FIG. 17 is a flowchart of the osteoporosis diagnostic support apparatus according to the first embodiment of the present invention.

Next, detailed operation of the cortical bone coarseness calculation unit 43 will be described. As shown in FIG. 17, the cortical bone coarseness calculation unit 43 (related to step S40) includes a function to implement the following steps.

<Determination of Measurement Reference Points> (S41)
<Acquisition of Profiles> (S42)
<Line Segment Extraction Using Line-Convergence Index Filter> (S43)
<Line Segment Area Calculation> (S44)
<Coarseness Measurement> (S45)

These steps will be described in detail below. Note that the numeric values cited in the description are desirable examples, but are not restrictive, and that numeric values may be selected, as appropriate, according to conditions of the image or accuracy of diagnostic support.

A technique similar to that of the cortical bone thickness calculation unit 42 is used in steps up to determination of measurement reference points and acquisition of profiles.

<Line Segment Extraction Using Line-Convergence Index Filter>

In applying the line-convergence index filter, in the case of coarseness calculation, as with thickness calculation, when the output C of the line-convergence index filter is 0.50 or less, the output is assumed to be C=0. Note that in the case of coarseness detection, changes can be made, such as lowering the threshold, by taking conditions of the image into consideration.

<Line Segment Area Calculation>

FIGS. 18A and 18B are images obtained before and after application of the line-convergence index filter, where FIG. 18A on the left is an image before application while FIG. 18B on the right is an image after application. These are digitized images obtained by setting C<0.50 to C=0, and C>=0.50 to C=1. After application of the line-convergence index filter, the sum total of positive pixels in the digitized image obtained by using C=0.50 as a threshold is calculated. There are two ROIs (regions of interest), on the right and left, and thus the result may be obtained by taking an average of positive pixel counts on the right and left or using the smaller of the positive pixel counts on the right and left.

<Coarseness Measurement>

The degree of coarseness of the cortical bone is determined based on whether the sum total of positive pixels is large or small. FIGS. 19A and 19B are examples of result images, where FIG. 19A is an example in which there are lots of coarse structures and osteoporosis is suspected while FIG. 19B is an example in which there is no coarse structure and the patient is considered normal.

The coarseness information about this cortical bone is displayed on the display apparatus 70, supporting a physician in making an osteoporotic diagnosis or is compared with data stored in the osteoporosis diagnostic support database, which is part of the osteoporosis diagnostic support unit 45, making it possible to judge the progress of osteoporosis and support osteoporotic diagnosis.

Note that the cortical bone thickness calculation unit 42 and cortical bone coarseness calculation unit 43 described so far may be used separately or may be used in combination.

Also, a cortical bone coarse structure calculation unit may be provided as the cortical bone condition calculation unit. Approximate osteoporotic diagnosis can also be supported based on whether there are line segments attributable to a coarse structure inside or outside the cortical bone.

Next, an osteoporosis diagnostic support apparatus according to a second embodiment in another aspect of the present invention will be described. Note that description will be given below schematically to the extent necessary to achieve the object of the present invention, that description will be given mainly to the extent necessary to describe appropriate parts of the present invention, and that description related to known techniques will be omitted.

Figure 20:
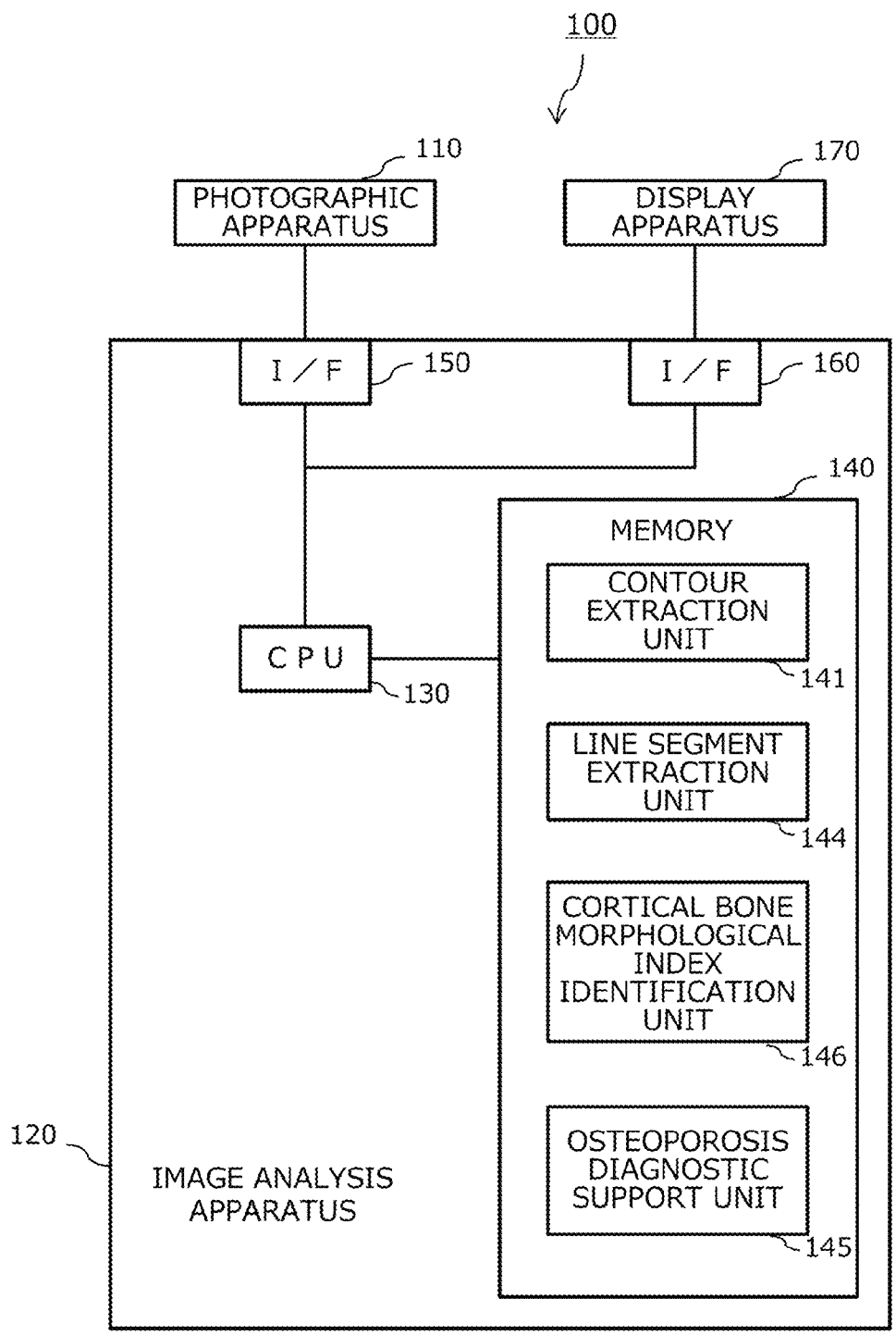
FIG. 20 is a block diagram of an osteoporosis diagnostic support apparatus according to a second embodiment of the present invention.

FIG. 20 is a block diagram of the osteoporosis diagnostic support apparatus according to the second embodiment of the present invention. As shown in FIG. 20, the osteoporosis diagnostic support apparatus 100 includes a photographic apparatus 110 adapted to shoot subject images of patients or the like, an image analysis apparatus 120 adapted to analyze images shot by the photographic apparatus 110, and a display apparatus 170 adapted to display the images shot by the photographic apparatus 110 and information obtained by the image analysis apparatus 120, where these apparatus are linked together by wired and/or wireless connections.

The image analysis apparatus 120 includes a CPU 130, a memory 140, and interfaces 150 and 160, which are linked, for example, as shown in FIG. 20. The memory 140 includes a contour extraction unit 141, a line segment extraction unit 144, a mandibular cortical bone morphological index identification unit 146, and an osteoporosis diagnostic support unit 45.

A panoramic X-ray imaging apparatus, which is a type of the photographic apparatus 110, is an apparatus adapted to shoot panoramic images in the dental area with X-rays. Various types of panoramic X-ray imaging apparatus have been put to practical use and any of them may be adopted. Note that the photographic apparatus 110 is not limited to the panoramic X-ray imaging apparatus, and any of a usual X-ray imaging apparatus, MRI/CT imaging apparatus, ultrasound imaging apparatus or a combination thereof may be adopted as the photographic apparatus 110. Appropriate diagnostic support may be provided by resulting images.

The panoramic image shot by the panoramic X-ray imaging apparatus serving as the photographic apparatus 110 is sent to the image analysis apparatus 120. The image analysis apparatus 120 analyzes images, being provided with computer resources including at least the CPU 130, memory 140, interface 150 with the photographic apparatus 110, interface 160 with the display apparatus 170 (described later). The computer resources may be provided in the form of a server or personal computer installed in close proximity, similar apparatus linked by wired and/or wireless connections, or Internet-based cloud.

The display apparatus 170 is connected to the image analysis apparatus 120 via the interface 160 and is capable of displaying the images shot by the photographic apparatus 110, images of a mandibular contour and line segments extracted by the image analysis apparatus 120, information about the morphological index and the like of the mandibular cortical bone identified by the image analysis apparatus 120, osteoporosis diagnostic support information obtained by the image analysis apparatus 120, and the like.

The contour extraction unit 141 is provided as a program stored in the memory 140 of the image analysis apparatus 120. The contour extraction unit 141 extracts a mandibular contour from a panoramic image. The mandibular contour is a portion which defines an outer edge of the lower jawbone.

Also, the line segment extraction unit 144 is provided as part of the image analysis apparatus 120. The line segment extraction unit 144, which is, for example, like a line-convergence index filter, is a program stored in the memory 140, and is capable of causing a computer to perform a function to extract line segments from a panoramic image.

Also, the mandibular cortical bone morphological index identification unit 146 is provided as part of the image analysis apparatus 120. The mandibular cortical bone morphological index identification unit 146, which also is a program stored in the memory 140, identifies the morphological index of the mandibular cortical bone based on results produced by either or both of the mandibular cortical bone contour extraction unit 141 and line segment extraction unit 144.

Furthermore, the osteoporosis diagnostic support unit 145 is provided as part of the image analysis apparatus 120, allowing identification results produced by the mandibular cortical bone morphological index identification unit 146 to be compared with data stored in the osteoporosis diagnostic support database (not shown), which is part of the osteoporosis diagnostic support unit 145.

Figure 21:
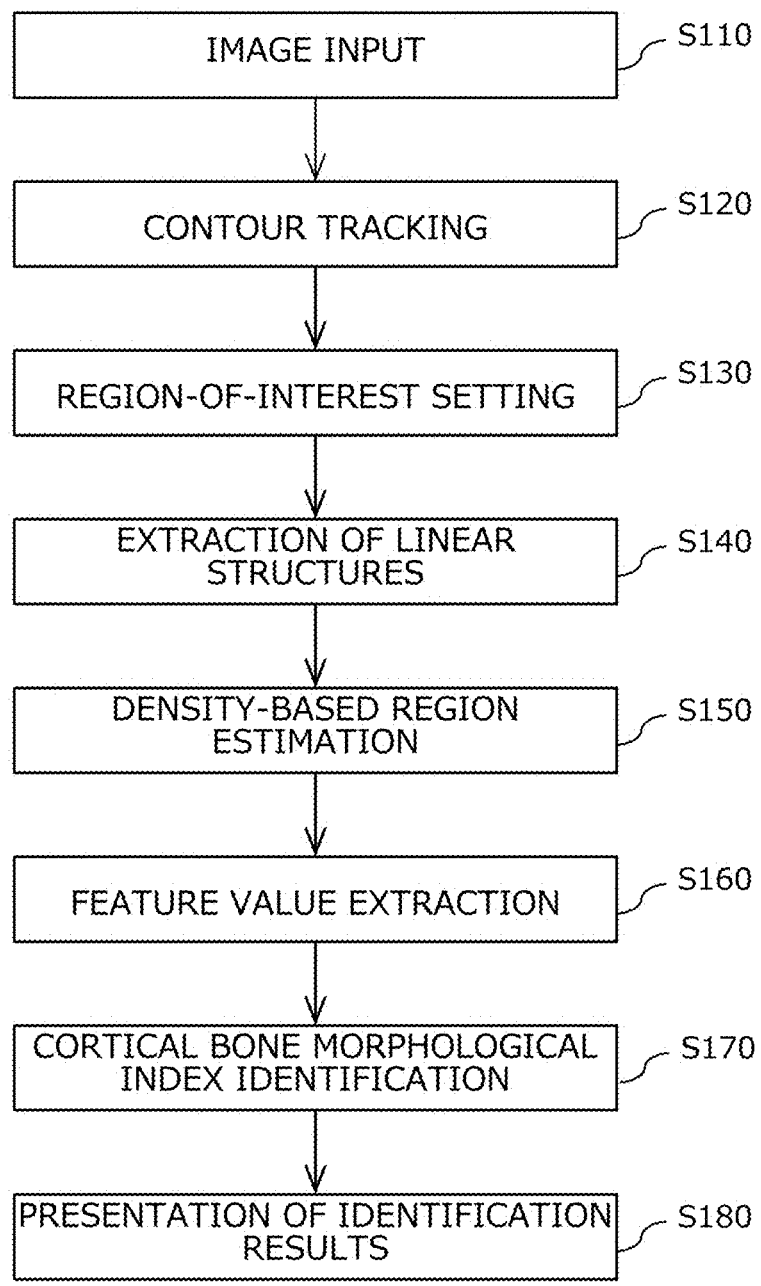
FIG. 21 is a flowchart of the osteoporosis diagnostic support apparatus according to the second embodiment of the present invention.

Now, operation of the osteoporosis diagnostic support apparatus configured as described above will be described. FIG. 21 is a flowchart of the osteoporosis diagnostic support apparatus according to the second embodiment of the present invention.

<Image Input> (S110)

First, images of the lower jawbone and surroundings thereof are inputted by being shot by a panoramic X-ray imaging apparatus, which is a type of the photographic apparatus 110. Here, details are similar to the image shooting according to the first embodiment.

<Contour Tracking> (S120)

Next, the shot panoramic image is inputted to the image analysis apparatus 120, and the mandibular contour is tracked by the contour extraction unit 141, which is part of the image analysis apparatus 120. Here, details are similar to the contour extraction according to the first embodiment.

<Region-of-Interest Setting> (S130)

Figure 22:
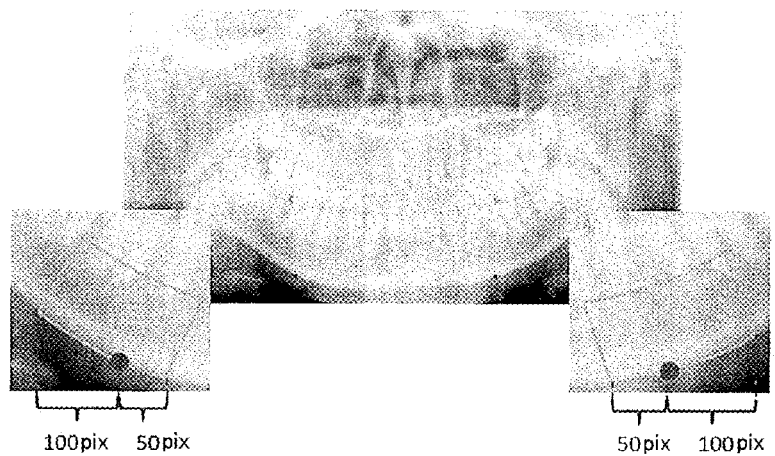
FIG. 22 is an explanatory diagram of a region of interest on the osteoporosis diagnostic support apparatus according to the second embodiment of the present invention.

Next, using the shot image and extracted contour, first, the mandibular cortical bone morphological index identification unit 146 sets a region of interest (ROI) containing the mandibular cortical bone. Here, details are similar to the determination of measurement reference points and acquisition of profiles according to the first embodiment, and the size of the region of interest is expanded to suite the identification of the mandibular cortical bone morphological index. That is, regions measuring 151 pixels wide along the mandibular contour (50 pixels from the respective measurement reference points in a medial direction and 100 pixels in an opposite direction) and 100 pixels high from the mandibular contour in the vertical direction are set, respectively, around the right and left measurement reference points as regions of interest. FIG. 22 shows an explanatory diagram of how to set regions of interest. Note that both height and width of 1 pixel correspond to 0.1 mm.

<Extraction of Linear Structures> (S140)

Figure 23:
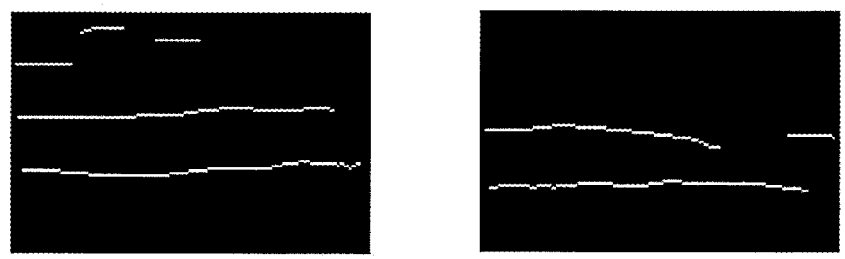
FIG. 23 is an explanatory diagram of linear structures on the osteoporosis diagnostic support apparatus according to the second embodiment of the present invention.

Then, using a line-convergence index filter, the mandibular cortical bone morphological index identification unit 146 extracts lines made up of linear structures (linear image formed by bone resorption) and a gray value peak of a dense cortical bone portion from the set regions of interest. Specifically, as described in the first embodiment, ridge lines are extracted and thinning and noise removal are performed as well using a line-convergence index filter, and then the ridge lines formed by gray value peaks of the cortical bone (ridge lines of the cortical bone) and the ridge lines formed by gray value peaks of coarse structure (ridge lines of coarse structure) are detected. Images of linear structures after application of a line-convergence index filter are shown in FIG. 23.

<Density-Based Region Estimation> (S150)

Figure 24A:
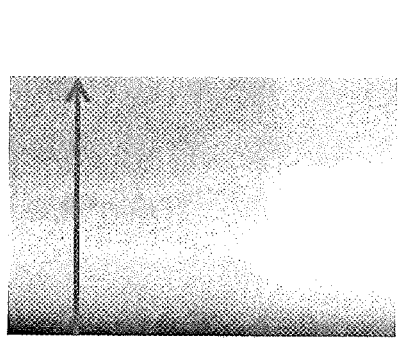
FIGS. 24A and 24B are explanatory diagrams of profile acquisition on the osteoporosis diagnostic support apparatus according to the second embodiment of the present invention.
Figure 24B:
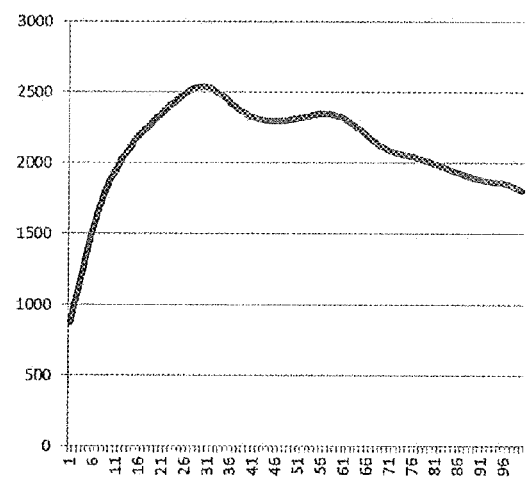
Figure 25:
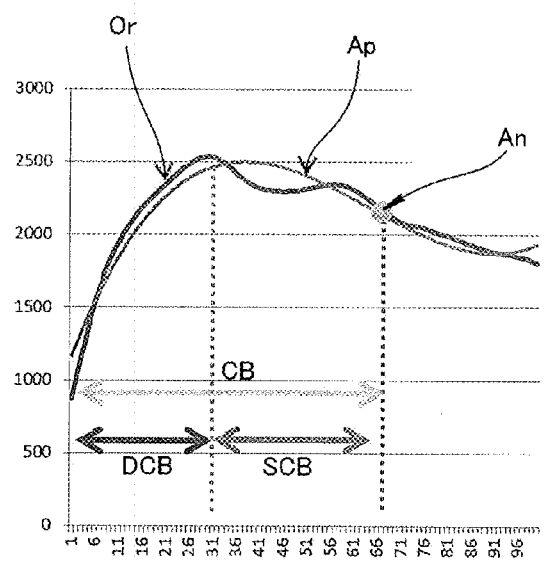
FIG. 25 is an explanatory diagram of region estimation on the osteoporosis diagnostic support apparatus according to the second embodiment of the present invention.
Figure 26:
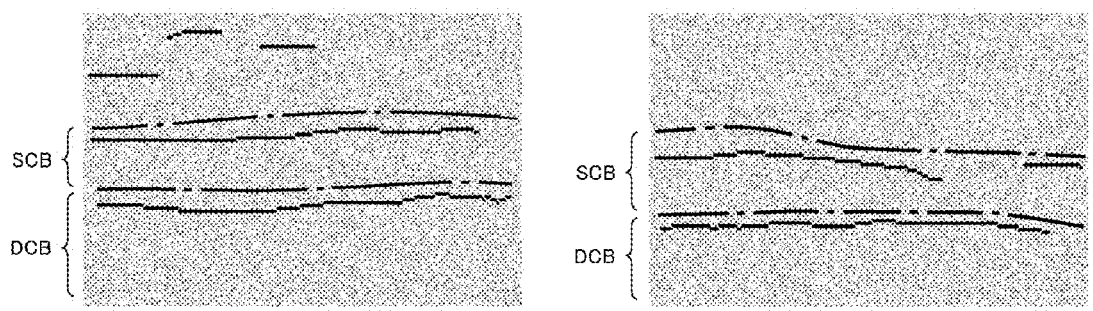
FIG. 26 is an explanatory diagram showing results of region estimation on the osteoporosis diagnostic support apparatus according to the second embodiment of the present invention.

Next, the mandibular cortical bone morphological index identification unit 146 regards a line existing at the lowermost end (on the mandibular contour side) as a gray value peak of a dense cortical bone portion and estimates a region up to an upper end of the line to be a region of the dense cortical bone portion. Also, 151 profiles 100 pixels long in the vertical direction from a lower end of each region of interest is acquired. FIGS. 24A to 24B show how a profile is acquired. A profile 100 pixels long is acquired as shown in FIG. 24A and graphically displayed as shown in FIG. 24B, where the ordinate represents the gray value and the abscissa represents the lower end of each region of interest, i.e., the distance from the contour. Then, as shown in FIG. 25, a cubic polynomial approximation curve Ap of each original profile Or is acquired, and inflection points An of the curve Ap are estimated to belong to a boundary line between the entire cortical bone CB and the cancellous bone. Then, a region up to the boundary line between the entire cortical bone, excluding the region of the dense cortical bone portion DCB estimated earlier, and the cancellous bone is estimated to be a region of a coarse cortical bone portion SCB. FIG. 26 shows estimation results of the dense and coarse regions (whose boundaries are indicated by alternate long and short dash lines in the figure) in the region of interest estimated in this way.

<Feature Value Extraction> (S160)

Next, the mandibular cortical bone morphological index identification unit 146 extracts feature values for use to identify the morphological index (type I, type II, or type III). Regarding the feature values, the following five types are used:

(1) the feature value of thickness,
(2) the number of pixels of line elements in a dense cortical bone region,
(3) the number of pixels of line elements in a coarse cortical bone region,
(4) the area of a coarse cortical bone region, and (5) the ratio of the average concentration value of line elements between the cortical bone regions.

Figure 27:
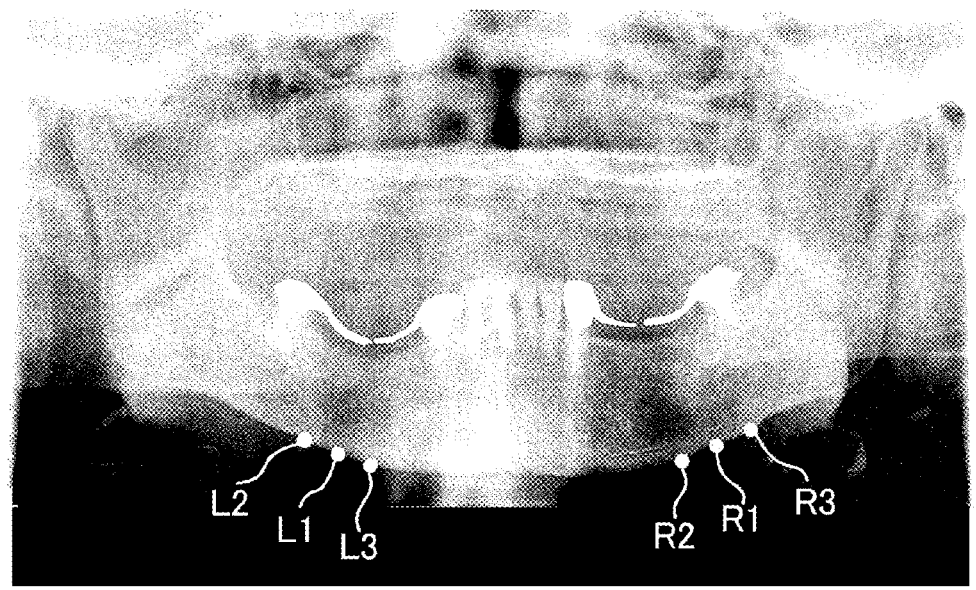
FIG. 27 is an explanatory diagram showing measurement reference points on the osteoporosis diagnostic support apparatus according to the second embodiment of the present invention.

Regarding the feature value of thickness, three measurement reference points each are set for a total of six points on the left and right of the lower jawbone to determine a general thickness of the cortical bone. As shown in FIG. 27, first, one each of measurement reference points L1 and R1 is set on the left and right, and then measurement reference points L2, L3, R2, and R3, two each on both sides, are set at intervals of 101 pixels from the respective measurement reference points L1 and R1 along the mandibular contour. A function equivalent to that of the cortical bone thickness calculation unit 42 according to the first embodiment is incorporated in the mandibular cortical bone morphological index identification unit 146 and used to measure the cortical bone thickness at each of the measurement reference points, and then the average value of measurement results at four locations are used as the feature value of thickness by excluding minimum and maximum values from six measured values by taking error values into consideration.

Figure 28:
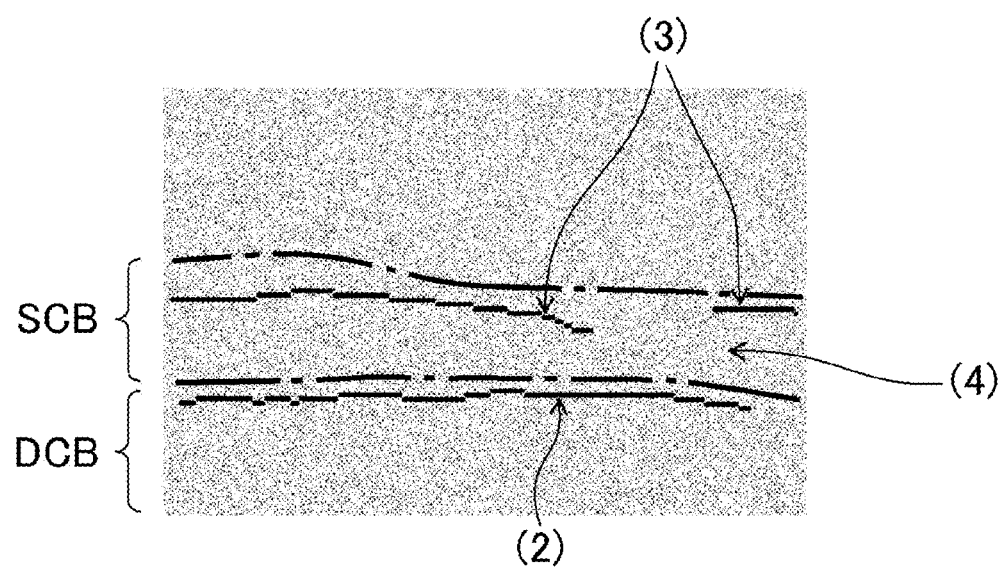
FIG. 28 is an explanatory diagram showing feature values of the osteoporosis diagnostic support apparatus according to the second embodiment of the present invention.

Next, feature values (2) to (4) are calculated using the diagram generated in the density-based region estimation. Specifically, as shown in FIG. 28, (2) the number of pixels of line elements in a dense cortical bone region, (3) the number of pixels of line elements in a coarse cortical bone region, and (4) the area of a coarse cortical bone region are determined.

Next, feature value (5) is the ratio of the average concentration value of line elements between the dense and coarse cortical bone regions. For example, if the average concentration value of pixels containing line elements in the dense cortical bone region is 3453 and a similar average concentration value in the coarse cortical bone region is 3212, the ratio between the average concentration values is 0.93 (3212/3453).

Here, because the area of a coarse region varies with the extent of coarseness, the area of a coarse cortical bone region is considered to be especially useful as a feature value for use to identify the morphological index (type I, type II, or type III).

<Cortical Bone Morphological Index Identification> (S170)

Next, the mandibular cortical bone morphological index identification unit 146 identifies the form of the cortical bone based on the feature values. A support vector machine (SVM), which is one of identification techniques based on "supervised learning," is used for the identification. SVM is one of the learning models which has the best identification performance.

Specifically, as shown in FIG. 29, when feature values (1) to (5) are found, for example, for 63 cases (learning samples), and these cases are classified into type I, type II, and type III of the morphological index according to physician's diagnosis, a separating hyperplane with a maximized margin can be determined from the feature values by the application of SVM, making it possible to identify the morphological index of a new case (unlearned sample) with high accuracy.

Note that although it has been stated in the above description that a support vector machine (SVM), which is one of identification techniques based on "supervised learning," is used for the identification of the form of the cortical bone, any other identification technique, such as Random Forest, Boosting, or Neural Network, may be used rather than SVM as long as the morphological index can be identified appropriately based on a large number of feature values.

<Presentation of Identification Results> (S180)

Finally, identification (classification) results of the morphological index are presented on the display apparatus 170, and the osteoporosis diagnostic support unit 145 supports physician's diagnosis of osteoporosis.

Note that although it has been stated in the above description that there are five feature values, one or more of them may be used rather than all the five and furthermore that feature values may be usefully added to improve accuracy of identification.

In particular, there is a technique which uses texture analysis, and 88 (4 angles×2 regions of interest×11 types) feature values made up of combinations of the following items were extracted based on the technique.

Distance: 5 pixels

Angles: 0, 45, 90, and 135 degrees (angles used to create a density co-occurrence matrix)

Regions of interest: entire cortical bone, and only coarse cortical bone region

Types: contrast, correlation, variance, entropy, sum entropy, inverse difference moment, sum average, sum variance, difference variance, difference entropy, angular second moment The effectiveness of these items was checked by determining coefficients of correlation with bone density, and it was found that the following 14 feature values were effective.

0-, 45-, 90-, or 135-degree variance of a coarse cortical bone region,

0-, 45-, 90-, or 135-degree difference variance of a coarse cortical bone region, 45-, 90-, or 135-degree difference entropy of a coarse cortical bone region, 0-degree inverse difference moment of all cortical bone regions, 0-degree difference entropy of all the cortical bone regions, 0-degree difference variance of all the cortical bone regions, Thus, in the cortical bone morphological index identification step described earlier, all or one or more of the 14 feature values may be used in addition to, or instead of, the five feature values described earlier. It can be expected that this will improve the accuracy of identification.

Also, although it has been stated in the above description that the morphological index of the cortical bone is classification into type I, type II, or type III, bone density may be estimated alternatively.

Specifically, when SVM was applied to the learning samples and regression analysis was conducted using Leave-one-out using the 5 feature values used earlier for morphological index identification and all or one or more of the 14 feature values as well as the bone density measured by an existing bone density measurement such as DXA as learning samples, a correlation was found with high reliability. Using this, bone density in a new case (unlearned sample) can be estimated with high reliability. Since density can be estimated at a specific numeric value, this will help greatly in providing support for physician's osteoporotic diagnosis.

REFERENCE SIGNS LIST

1 Osteoporosis diagnostic support apparatus
10 Photographic apparatus
20 Image analysis apparatus
30 CPU
40 Memory
41 Contour extraction unit 42 Cortical bone thickness calculation unit
43 Cortical bone coarseness calculation unit
44 Line segment extraction unit
45 Osteoporosis diagnostic support unit
50 Interface
60 Interface
70 Display apparatus
100 Osteoporosis diagnostic support apparatus
110 Photographic apparatus
120 Image analysis apparatus
130 CPU
140 Memory
141 Contour extraction unit
144 Line segment extraction unit
145 Osteoporosis diagnostic support unit
146 Cortical bone morphological index identification unit
150 Interface
160 Interface
170 Display apparatus

The invention claimed is:

1. An osteoporosis diagnostic support apparatus comprising:
  a contour extraction unit adapted to extract a mandibular contour from an image of a mandibular cortical bone photographed by a photographic apparatus adapted to photograph the mandibular cortical bone and surroundings thereof;
  a line segment extraction unit adapted to extract line segments from the image of the mandibular cortical bone photographed by the photographic apparatus, where the line segments are formed by a gray level distribution and include line segments of the cortical bone; and
  a cortical bone thickness calculation unit adapted to calculate a thickness of the cortical bone based on the extracted mandibular contour and line segments, wherein
  the cortical bone thickness calculation unit determines a measurement reference point based on the mandibular contour extracted by the contour extraction unit, acquires profiles from the determined measurement reference point by establishing plural points at predetermined intervals around each measurement reference point on the mandibular contour, acquiring a perpendicular line from each of the points to the mandibular contour, and finding gray values at predetermined intervals on the perpendicular line, the gray values being gained by determining pixel values pixel-by-pixel on the perpendicular line and by being converted into images, selects an optimum group of the profiles by selecting a profile group which maximizes the sum total ΣD decrease widths, the decrease widths being determined as a difference between the gray value at a search start point and the smallest gray value in a search range of the profile, and thereby calculates the thickness of the cortical bone from the selected optimum group of the profiles by determining the gradients Ai of the profile at each of points beginning with a measurement start point, calculating an average Aave of only the gradients associated with decreasing gray values, determining a point Tresult closest to the start point which satisfies the condition of Ai<Aave, and designating the distance from the measurement start point to Tresult as the thickness of the cortical bone.

2. The osteoporosis diagnostic support apparatus according to claim 1, wherein the line segment extraction unit uses a line-convergence index filter in extracting the line segments.

3. The osteoporosis diagnostic support apparatus according to claim 1, wherein the determination of the measurement reference point in the cortical bone thickness calculation unit includes detecting a mandibular angle.

4. An osteoporosis diagnostic support program stored in a memory configured to perform a computer function, the program comprising:
  contour extraction means for extracting a mandibular contour from an image of a mandibular cortical bone photographed by a photographic apparatus adapted to photograph the mandibular cortical bone and surroundings thereof;
  line segment extraction means for extracting line segments from the image of the mandibular cortical bone photographed by the photographic apparatus, where the line segments are formed by a gray level distribution and include line segments of the cortical bone;
  cortical bone thickness calculation means for calculating a thickness of the cortical bone based on the extracted mandibular contour and line segments, wherein
  the osteoporosis diagnostic support program causes the cortical bone thickness calculation means to determine a measurement reference point based on the mandibular contour extracted by the contour extraction means, acquire profiles from the determined measurement reference point by establishing plural points at predetermined intervals around each measurement reference point on the mandibular contour, acquiring a perpendicular line from each of the points to the mandibular contour, and finding gray values at predetermined intervals on the perpendicular line, the gray values being gained by determining pixel values pixel-by-pixel on the perpendicular line and by being converted into images, select an optimum group of the profiles by selecting a profile group which maximizes the sum total ΣD decrease widths, the decrease widths being determined as a difference between the gray value at a search start point and the smallest gray value in a search range of the profile, and thereby calculate the thickness of the cortical bone from the selected optimum group of the profiles by determining the gradients Ai of the profile at each of points beginning with a measurement start point, calculating an average Aave of only the gradients associated with decreasing gray values, determining a point Tresult closest to the start point which satisfies the condition of Ai<Aave, and designating the distance from the measurement start point to Tresult as the thickness of the cortical bone.

5. The osteoporosis diagnostic support program according to claim 4, wherein the line segment extraction means uses a line-convergence index filter in extracting the line segments.

6. The osteoporosis diagnostic support program according to claim 4, wherein the determination of the measurement reference point in the cortical bone thickness calculation means includes detecting a mandibular angle.

* * * * *

UNITED STATES PATENT AND TRADEMARK OFFICE
CERTIFICATE OF CORRECTION

PATENT NO. : 10,004,448 B2  
APPLICATION NO. : 15/162447  
DATED : June 26, 2018  
INVENTOR(S) : Tsuji et al.

Page 1 of 1

It is certified that error appears in the above-identified patent and that said Letters Patent is hereby corrected as shown below:

On the Title Page

On (73) Assignee, add "Gifu University, Gifu (JP)"

Signed and Sealed this  
Sixteenth Day of July, 2019

Andrei Iancu  
*Director of the United States Patent and Trademark Office*